United States Patent
Niedospial, Jr.

(10) Patent No.: US 6,179,822 B1
(45) Date of Patent: Jan. 30, 2001

(54) SINGLE USE UNIVERSAL ACCESS DEVICE/ MEDICAL CONTAINER ASSEMBLY

(75) Inventor: John J. Niedospial, Jr., Burlington, NJ (US)

(73) Assignee: Bracco Research USA, Princeton, NJ (US)

(*) Notice: Under 35 U.S.C. 154(b), the term of this patent shall be extended for 0 days.

(21) Appl. No.: 09/246,152

(22) Filed: Feb. 8, 1999

Related U.S. Application Data

(63) Continuation-in-part of application No. 09/009,487, filed on Jan. 20, 1998, now Pat. No. 6,019,751.

(51) Int. Cl.⁷ ............................ A61B 19/00; A61B 17/06; B65D 39/00
(52) U.S. Cl. ........................ 604/408; 604/415; 215/247; 215/249; 206/438; 206/828
(58) Field of Search .................... 607/403, 408, 607/411–415, 905; 215/247, 249; 206/828, 438

(56) References Cited

U.S. PATENT DOCUMENTS

| | | |
|---|---|---|
| Re. 32,065 | 1/1986 | Ralston et al. . |
| 2,619,277 | 11/1952 | Shumann . |
| 4,088,166 | 5/1978 | Miller . |
| 4,150,744 | 4/1979 | Fennimore . |
| 4,509,197 | 4/1985 | Long . |
| 4,548,605 | 10/1985 | Iwamoto et al. . |
| 4,660,721 | 4/1987 | Mykleby . |
| 4,872,553 | 10/1989 | Suzuki et al. . |
| 4,892,537 | 1/1990 | Carmen et al. . |
| 4,976,707 | 12/1990 | Bodicky et al. . |
| 5,071,413 | 12/1991 | Utterberg . |
| 5,086,915 | 2/1992 | Yashima et al. . |
| 5,088,994 | 2/1992 | Porat . |
| 5,360,413 | 11/1994 | Leason et al. . |
| 5,391,150 | 2/1995 | Richmond . |
| 5,423,794 | 6/1995 | Adolf et al. . |
| 5,540,674 * | 7/1996 | Karas et al. ............................ 604/415 |
| 5,573,516 | 11/1996 | Tyner . |
| 5,728,086 * | 3/1998 | Niedospial, Jr. ......................... 604/408 |
| 5,728,087 | 3/1998 | Niedospial, Jr. . |
| 5,738,671 * | 4/1998 | Niedospial, Jr. et al. ............ 604/408 |
| 5,779,693 * | 7/1998 | Ropiak et al. ........................... 604/408 |
| 5,817,082 * | 10/1998 | Niedospial, Jr. et al. ............ 604/414 |
| 5,902,298 * | 5/1999 | Niedospial, Jr. et al. ............ 604/414 |
| 5,941,866 * | 8/1999 | Niedospial, Jr. ......................... 604/408 |
| 5,984,912 * | 11/1999 | Niedospial, Jr. et al. ............ 604/408 |
| 6,019,751 * | 2/2000 | Gabbard et al. ........................ 604/408 |

* cited by examiner

Primary Examiner—Dennis Ruhl
(74) Attorney, Agent, or Firm—Imre Balogh

(57) ABSTRACT

Single use universal connector, flexible medical container assembly for the containment and delivery of medical fluid having three access means: a single use universal connector access means for luer connection, needle or spike piercing; a needle access means and a spike access means.

36 Claims, 32 Drawing Sheets

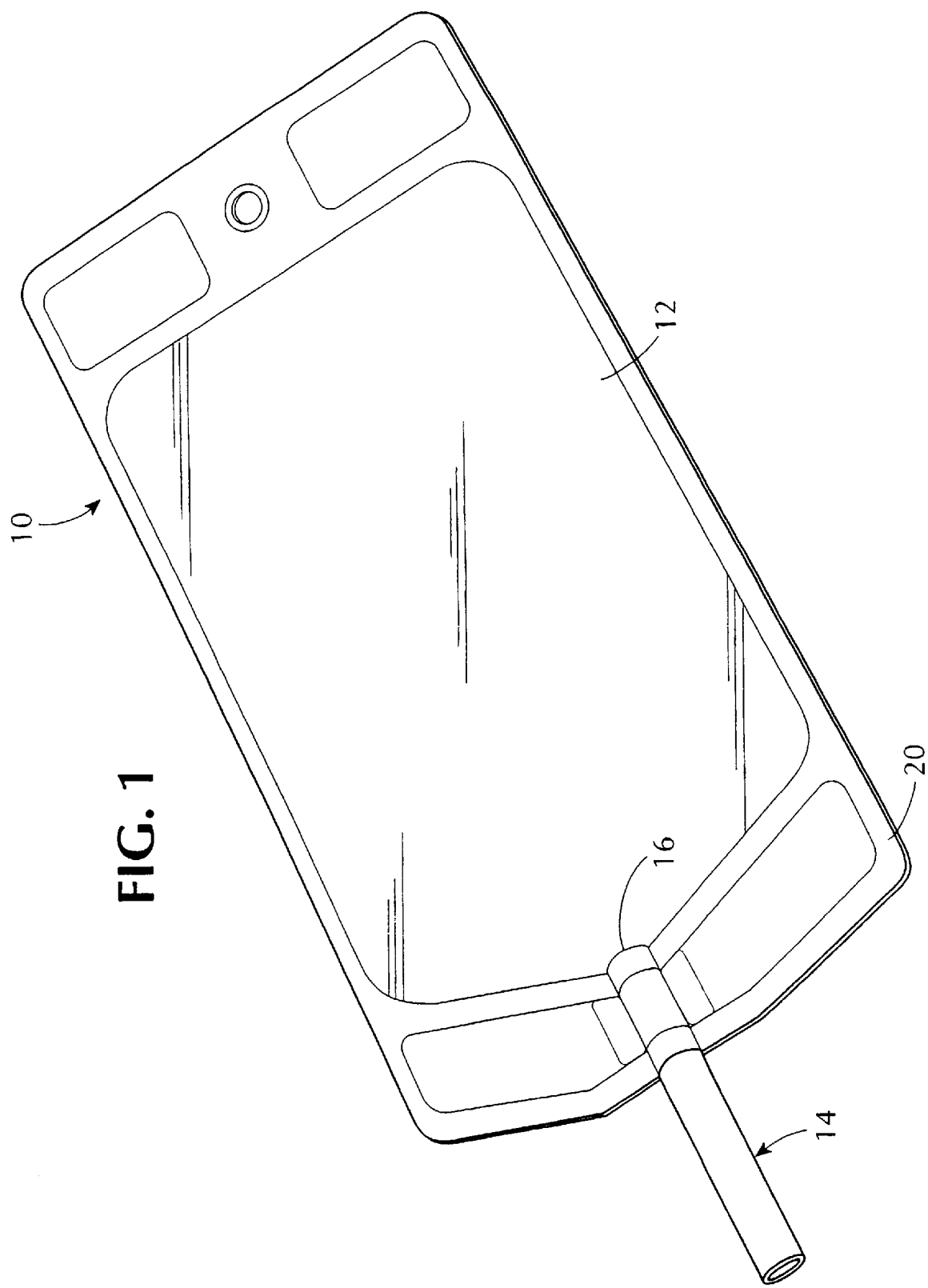

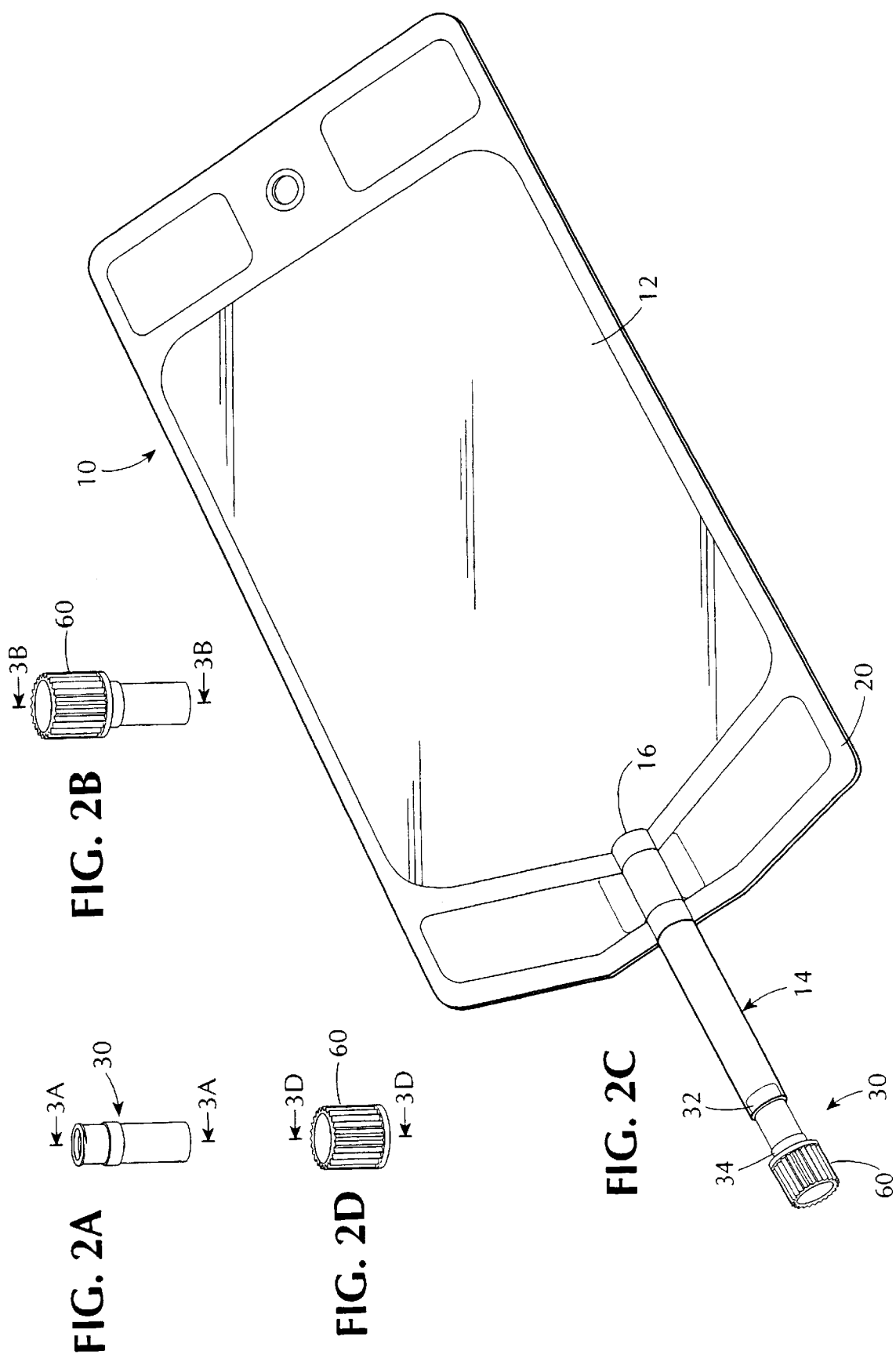

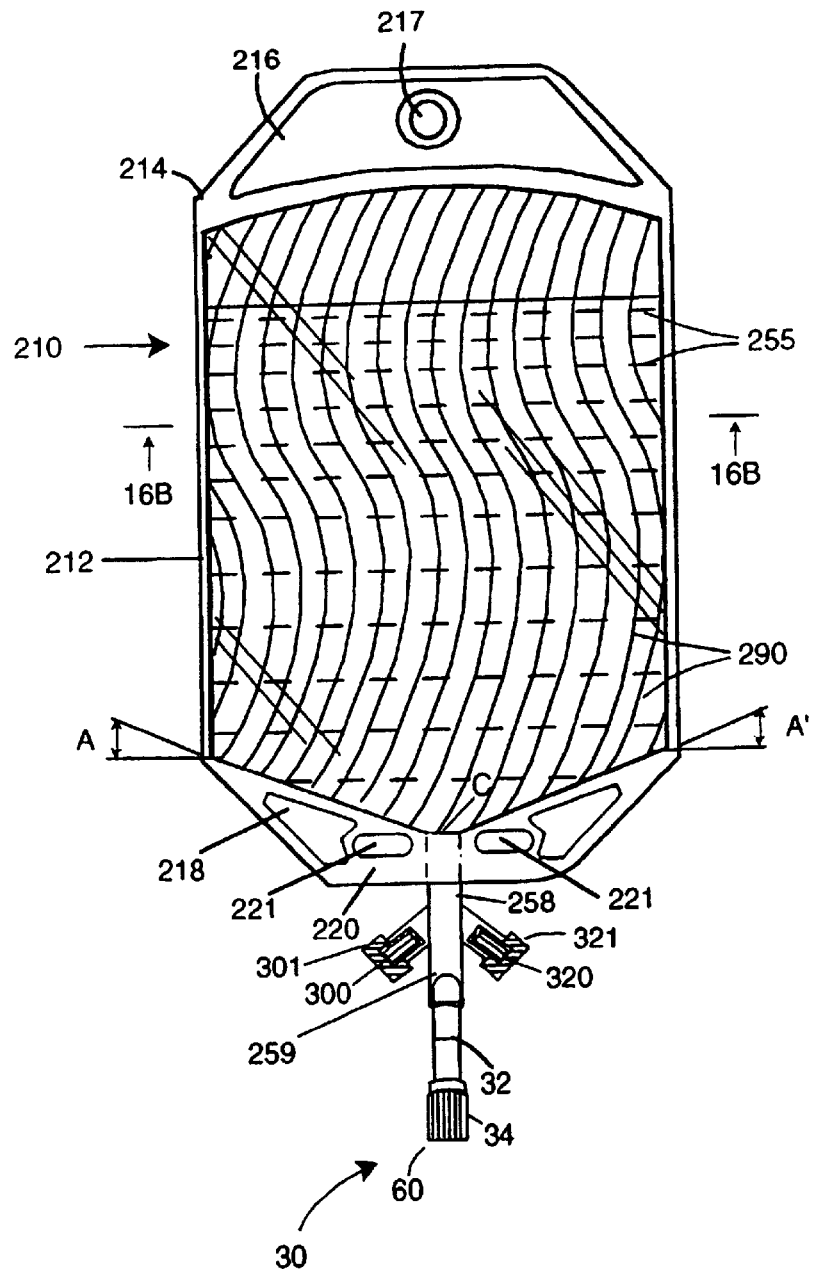

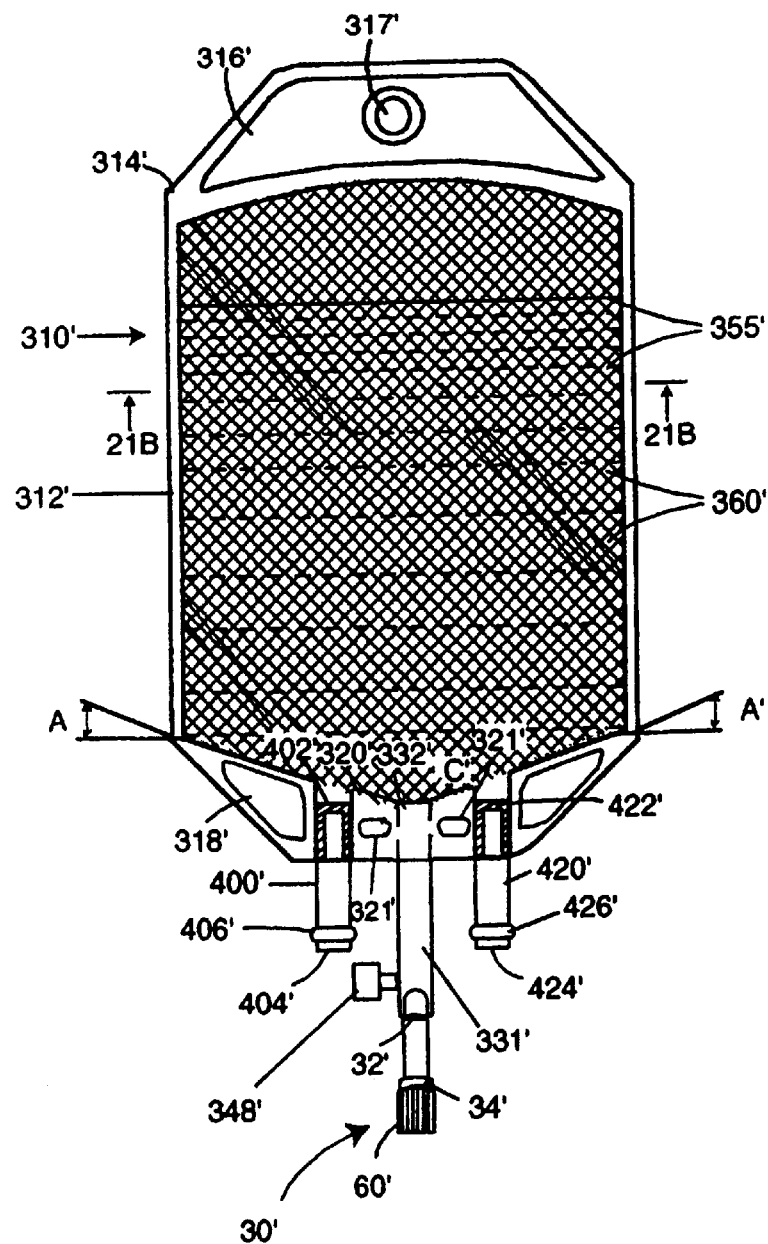
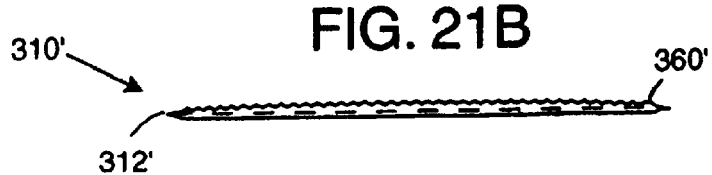

SINGLE USE UNIVERSAL ACCESS DEVICE/MEDICAL CONTAINER ASSEMBLY

This application is a continuation-in-part of application Ser. No. 09/009,487, filed Jan. 20, 1998 now U.S. Pat. No. 6,019,751.

BACKGROUND OF THE INVENTION

1. Field of the Invention

This invention relates to a single use universal connector connectable to containers having fluid contents therein designed for delivery to a site of administration. More particularly, the invention relates to a single use universal connector connectable to one or more exit ports of collapsible bags and bottles such as intravenous (IV) bags.

2. Reported Developments

Parenteral fluids, such as therapeutic drugs, diagnostic contrast media and nutrients are conventionally administered to a patient from a container, such as a collapsible bag or bottle having a fluid exit port. The fluid exit port may include means, such as a tube, spike or cannula, the distal end of which is in communication with the fluid content of the container and the proximal end of which is connected to the desired site on the patient. Conventionally, the proximal end of said means includes a needle that can puncture the skin of a patient. The fluid exit port is sealed by a membrane which is punctured by inserting a spike into the exit port when fluid delivery is desired. The membrane can also be a resealable membrane which after puncture reseals itself, due to its highly elastomeric properties, to prevent further fluid flow through the fluid exit port.

One approach used by the prior art to penetrate the membrane covering the fluid exit port comprises the use of syringes or spikes which carry the danger of accidental injuries caused by the sharp points of the needles and spikes. Such injuries accidentally inflicted on the health practitioner carry the further risk of getting infected with diseases such as AIDS. In order to reduce the danger of accidental injuries, spikes having relatively blunt tips were used. However, such pikes puncture a large area of the membrane and once the spikes are removed the membrane no longer seals the fluid exit port.

Another approach used by the prior art is the provision of a tubular member which is more blunt than a spike so that it is unlikely to penetrate the skin yet capable of penetrating the latex diaphragm type seals.

Still another approach used by the prior art is a valve positioned in the fluid exit port, the valve being operable by engagement with a spikeless or needleless IV component and contains a resilient valve disc positioned in the fluid passageway and blocks fluid flow when the disc is in the closed position, and allows fluid flow when the disc is in the open position.

Still another needleless connector of the prior art uses a resilient conical valve head in a housing. The conical valve head is positioned against the valve seat to form a seal. When the male fitting of a syringe, or some other device, is inserted into the inlet of the housing, it pushes the tip portion of the resilient valve head inwardly so that the valve head is deformed away from the valve seat thereby allowing fluid communication. In still other embodiments of the prior art, a needleless connector includes an elastomeric conical valve head biased against a conical valve seat by a helical spring to form a seal.

The above generally described devices have greatly reduced the risk of needle-stick associated injuries by use of syringes to withdraw medical fluids from collapsible bags and bottles.

However, there still exists the need to provide a universal connector which may be used with a wide variety of connection sites. A seal or diaphragm is a main component of the herein-described invention which does not require penetration by any sharp or even blunt object in order to establish fluid communication between the content of the container and the site of delivery.

SUMMARY OF THE INVENTION

In accordance with the present invention there is provided a single use universal connector which can be used to access the fluid content of a container or to transfer a fluid into the container. The single universal connector can be used in collapsible and non-collapsible bags, bottles and vials made of glass or polymeric material which contain a fluid exit port into which the universal connector is inserted sealing the fluid exit port. The fluid contained in the container may be a therapeutic liquid, diagnostic media or a nutritional formula which can be sterilized in bulk and then aseptically transferred into the container or it can be sterilized in the container stoppered with the universal connector. The single use universal connector is made of rigid or semi-rigid polymeric materials such as polyvinyl chloride, polyethylene and polypropylene.

The fluid in a container stoppered by the single use universal connector can be accessed by means well-known in the art, such as syringes having sharp or blunt needle cannulas. Preferably, the access means comprises a luer connector in order to prevent accidental injuries to health care workers and patients caused by the use of syringes.

The single use universal connector comprises:

(1) a connector body of tube-like configuration the distal end of which is designed to be slideably insertable into the fluid exit port, and the proximal end of which is designed to seal the content of the container by an elastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is of cylindrical, however, preferred embodiments of the present invention include dome-shape, cone-shape, conic-section elastomeric membranes which can be ruptured or pierced even more readily by blunt access means than the cylindrical configuration embodiment.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

Preferred medical containers used in combination with the single use universal connector are those disclosed in U.S.

Pat. Nos. 5,728,087 and 5,779,693 each of which is incorporated herein by reference in its entirety.

In one preferred embodiment, the universal, flexible, plastic container equipped with the single use universal connector of the present invention comprises:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all or at least portions of said interior of said pouch being mechanically deformed to prevent adhesion of said first an second plastic sheets; and (b) a combination access member of inverted Y shape configuration having:

b1) a stem with a proximal end and a distal end, said proximal end located at the bottom, center portion of the pouch sealed between the two sheets in the periphery thereof; and b2) a pair of tines having proximal and distal ends, the proximal ends thereof being integral with the stem of the access member;

the combination access member comprising:

(1) an IV access port at the distal end of the stem equipped with the single use universal connector sealably attached thereto;

(2) a needle access port located in one of the tines of the combination access member; and (3) a spike access port located in the other of the tines of the combination access member;

said needle and spike access ports being equipped with caps.

The single use universal connector comprises:

(1) a connector body of tube-like configuration the distal end of which is designed to be slideably insertable into the fluid exit port, and the proximal end of which is designed to seal the content of the container by an e lastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is of cylindrical, however, preferred embodiments of the present invention include dome-shape, cone-shape, conic-section elastomeric membranes which can be ruptured or pierced even more readily by blunt access means than the cylindrical configuration embodiment.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

This embodiment of the present invention provides: needle access and spike access through the respective access ports; it also provides IV access using the single use universal connector on the stem of the inverted Y shape member.

The stem of the combination access member is equipped with a vent, located preferably close to the proximal end thereof and spaced from the location of the tines.

Preferably the top portion at the periphery of the pouch comprises at least one hole for suspending the container when it is in use for delivering the content thereof to the delivery site, and the bottom portion at the periphery of the pouch comprises at least one, and preferably a plurality of holes to facilitate suspending the pouch during the filing process.

Another embodiment of the present invention comprises:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all, or at least portions of said interior of said pouch being mechanically deformed to prevent adhesion of said first and second plastic sheets;

b) an IV access port located in the center bottom portion of the pouch equipped with the single use universal connector sealably attached thereto;

c) a needle access port located on one side of the IV access port in the bottom portion of the pouch; and d) a spike access port located on the other side of the IV access port in the bottom portion of the pouch;

said needle and spike access ports being equipped with crimp seals.

Preferably the top portion at the periphery of the pouch comprises at least one hole for suspending the container when it is in use for delivering the content thereof to the delivery site, and the bottom portion at the periphery of the pouch comprises at least one, and preferably a plurality of holes to facilitate suspending the pouch during the filing process.

The embodiments of the universal flexible container of the present invention may be of any configuration, such as square, round, oval, hexagonal or octagonal. Typically, it is a generally rectangular configuration. The embodiments are designed for the containment and delivery of parenteral solutions, such as diagnostic contrast media, nutrients, and drug formulations to a patient in need of such parenteral solutions.

BRIEF DESCRIPTION OF THE DRAWINGS

FIGS. 1 to 7 show the single use universal connector in conjunction with a generalized rectangular medical bag designated in FIG. 1. Accordingly:

FIG. 1 is a perspective view of a medical bag;

FIG. 2A is a perspective view of the universal connector of the present invention without the cap attached;

FIG. 2B is a perspective view of the universal connector of the present invention with the cap attached;

FIG. 2C is a perspective view of the universal connector of the present invention with the cap attached and connected to the medical bag of FIG. 1;

FIG. 2D is a perspective view of the cap;

FIG. 3AA is a top plan view of the universal connector without the cap attached of FIG. 3A;

FIG. 3CC is a top plan view of the cap shown in FIG. 21);

FIG. 4 is a cross-sectional view of another embodiment of the universal connector with the cap attached, showing a rubber seal having a generally dome-shaped configuration in the center thereof;

FIG. 5 is a cross-sectional view of still another embodiment of the universal connector with the cap attached, showing a rubber seal having a large generally cone-shaped configuration in the center thereof;

FIG. 6 is a cross-sectional view of still another embodiment of the universal connector with the cap attached, showing a rubber seal having a small, generally conic section configuration in the center thereof;

FIG. 7 is a female luer connector attachable to the universal connector of the present invention;

FIG. 16A is a plan view of the flexible container shown in FIG. 8 one wall of which is embossed with vertically oriented S-shape channels;

FIG. 16B is a cross-section of the universal, flexible container shown in FIG. 16A taken along the line 16B—16B;

Figure 18:
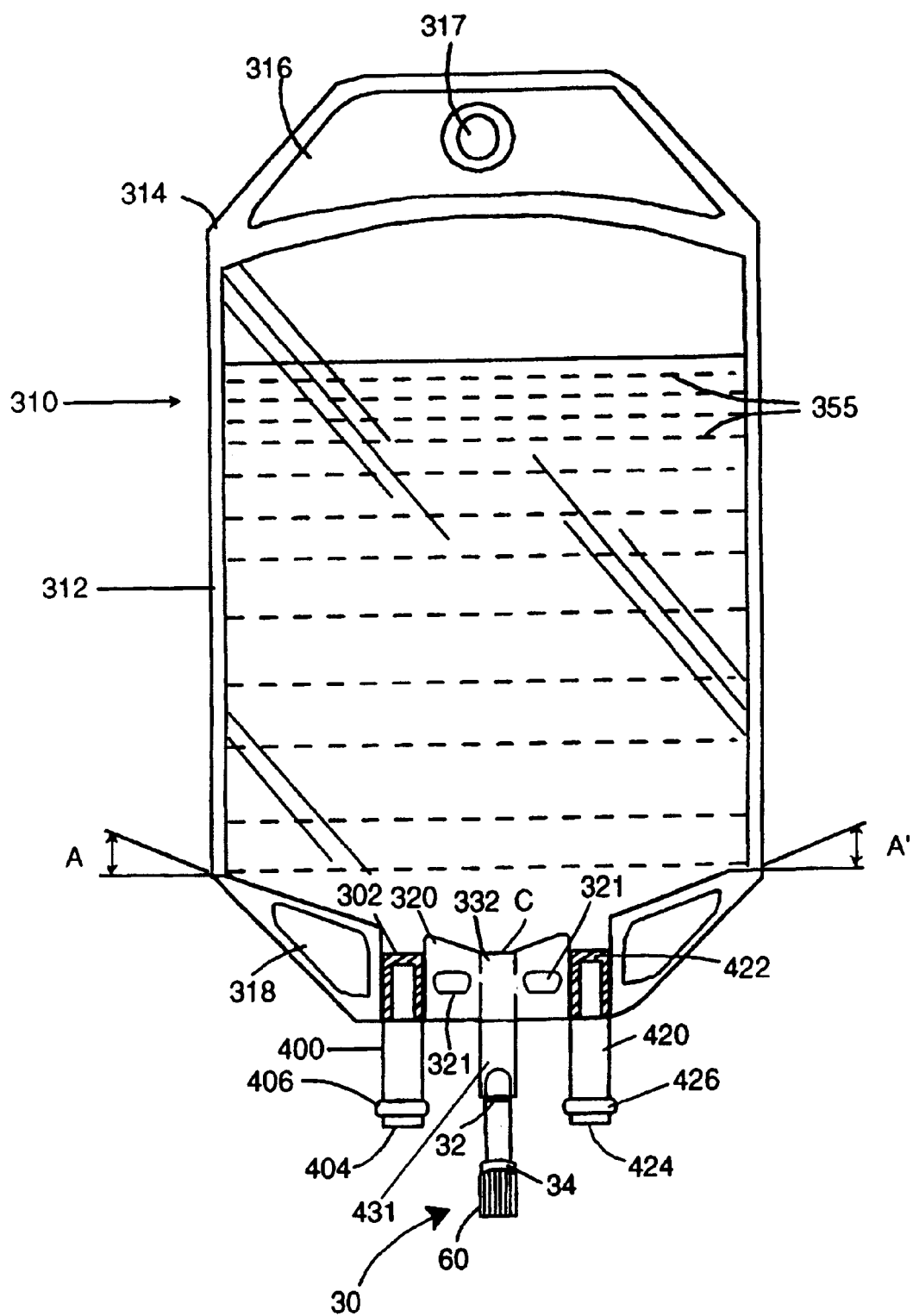
FIG. 18 is a plan view of a universal, flexible container showing:
 a) a pouch with an IV access port located in the center, bottom portion of the pouch equipped with the single use universal connector;
 b) a needle access port located in the bottom portion of the pouch on one side of the IV access port; and
 c) a spike access port located in the bottom portion of the pouch on the other side of the IV access port.
Figure 19:
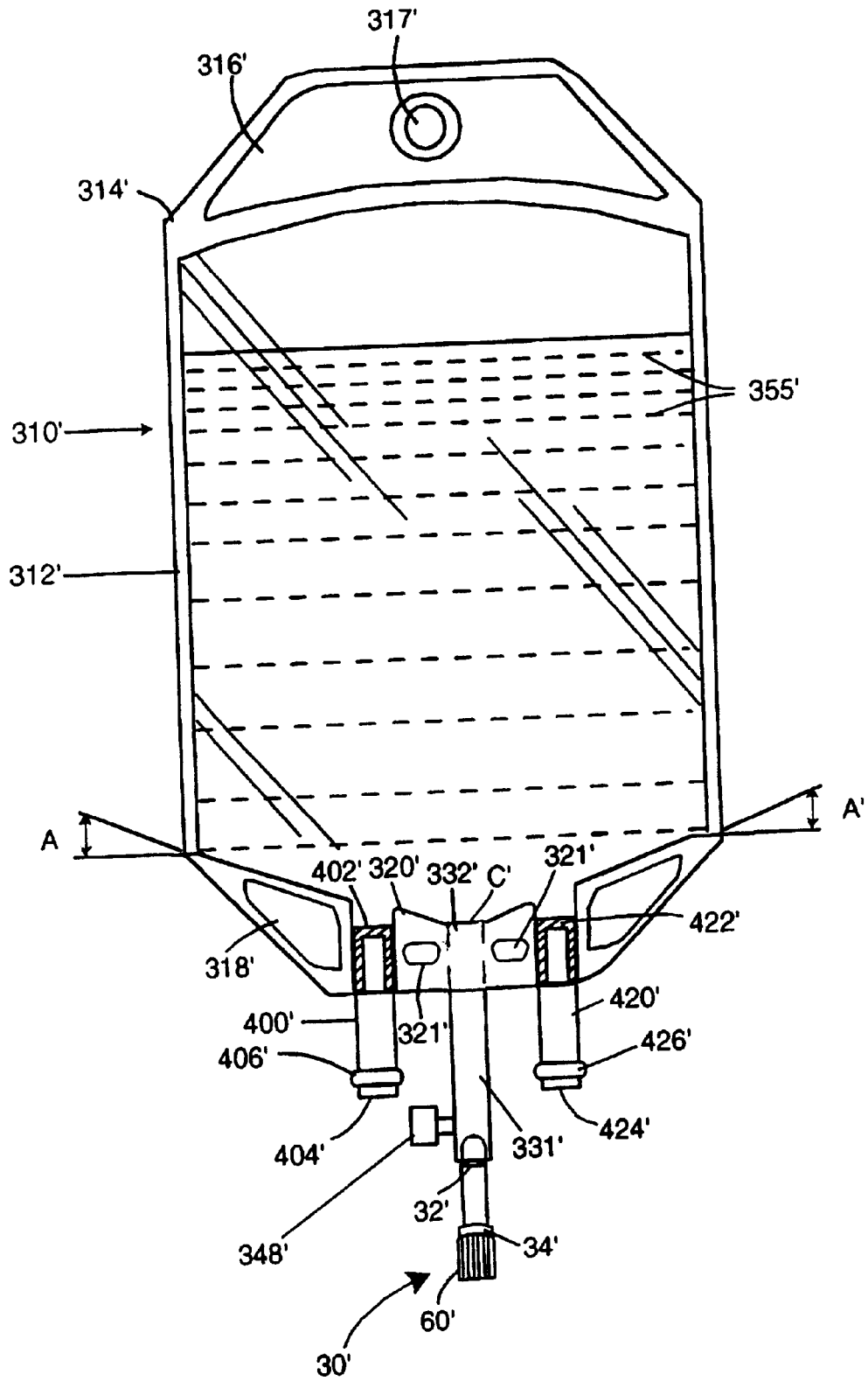
FIG. 19 is a plan view of another embodiment of the universal, flexible container showing:
 a) a pouch with an IV access port equipped with the single use universal connector and a vent at the proximal end thereof adjacent to the IV access port.
Figure 20A:
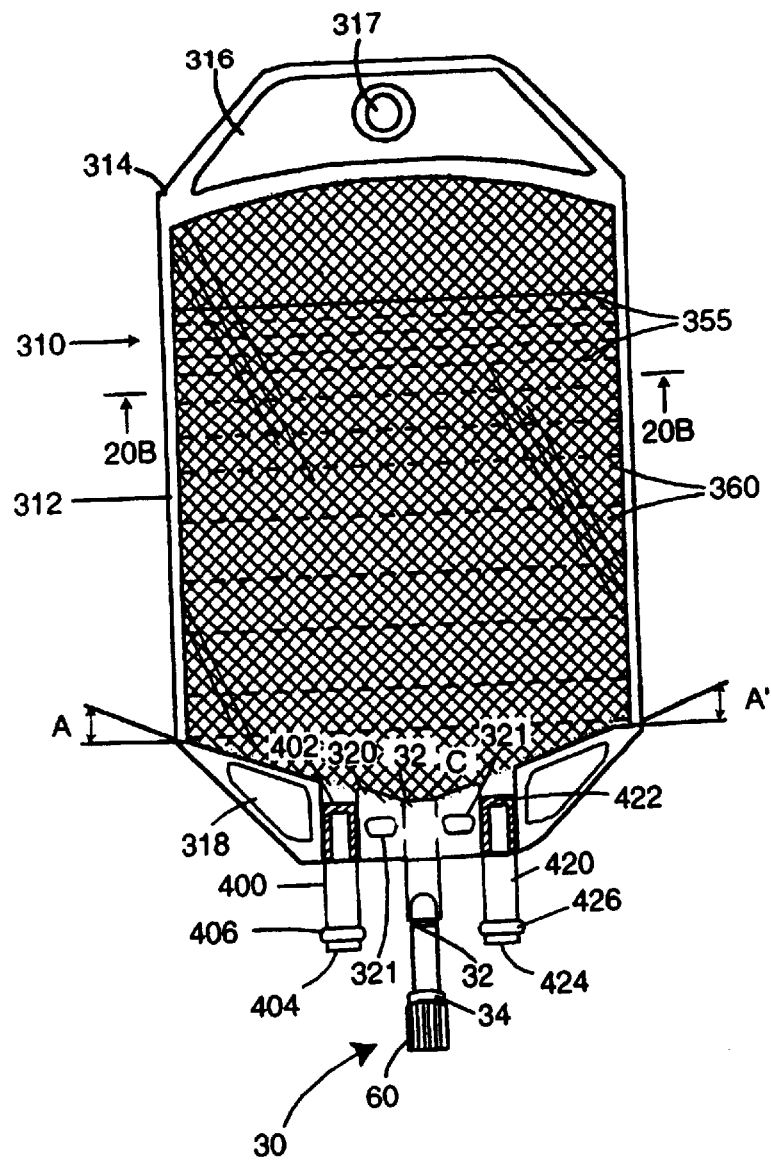
Figure 20B:
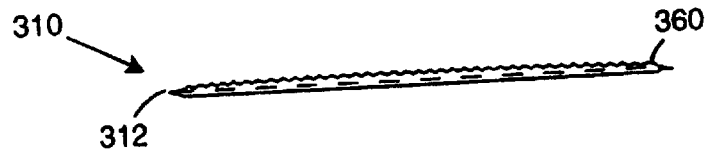
Figure 22A:
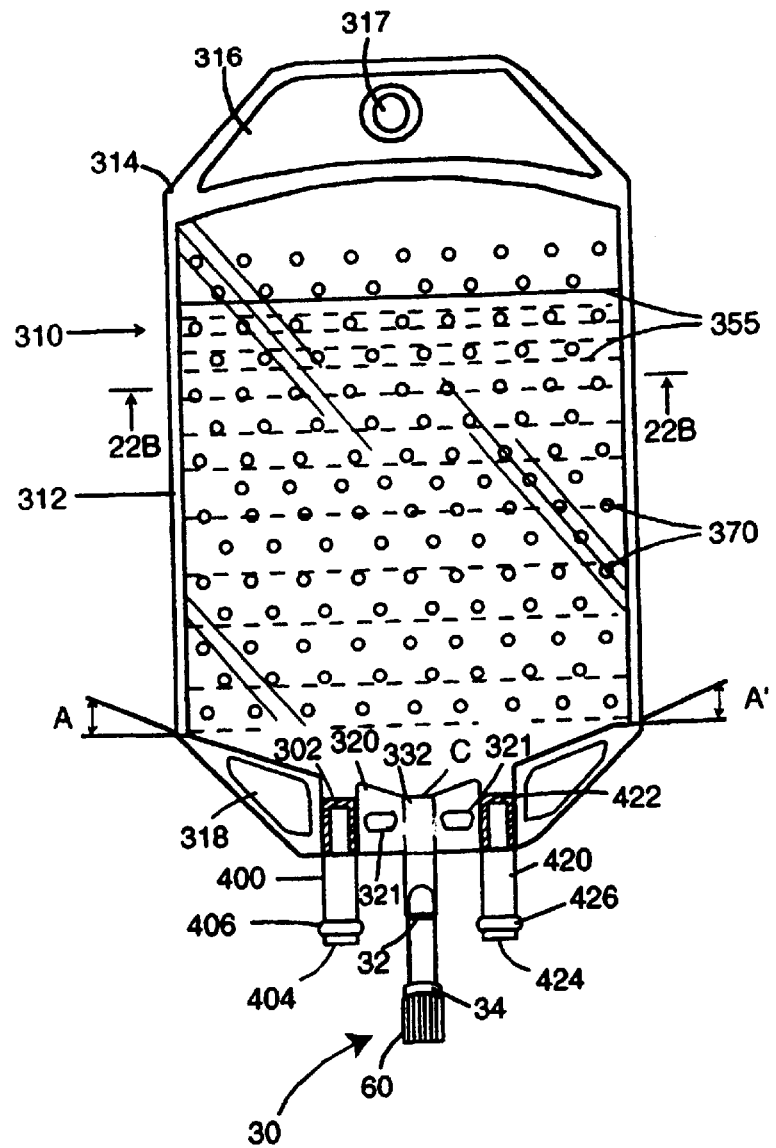
Figure 22B:
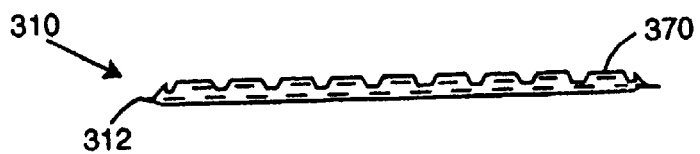
Figure 23A:
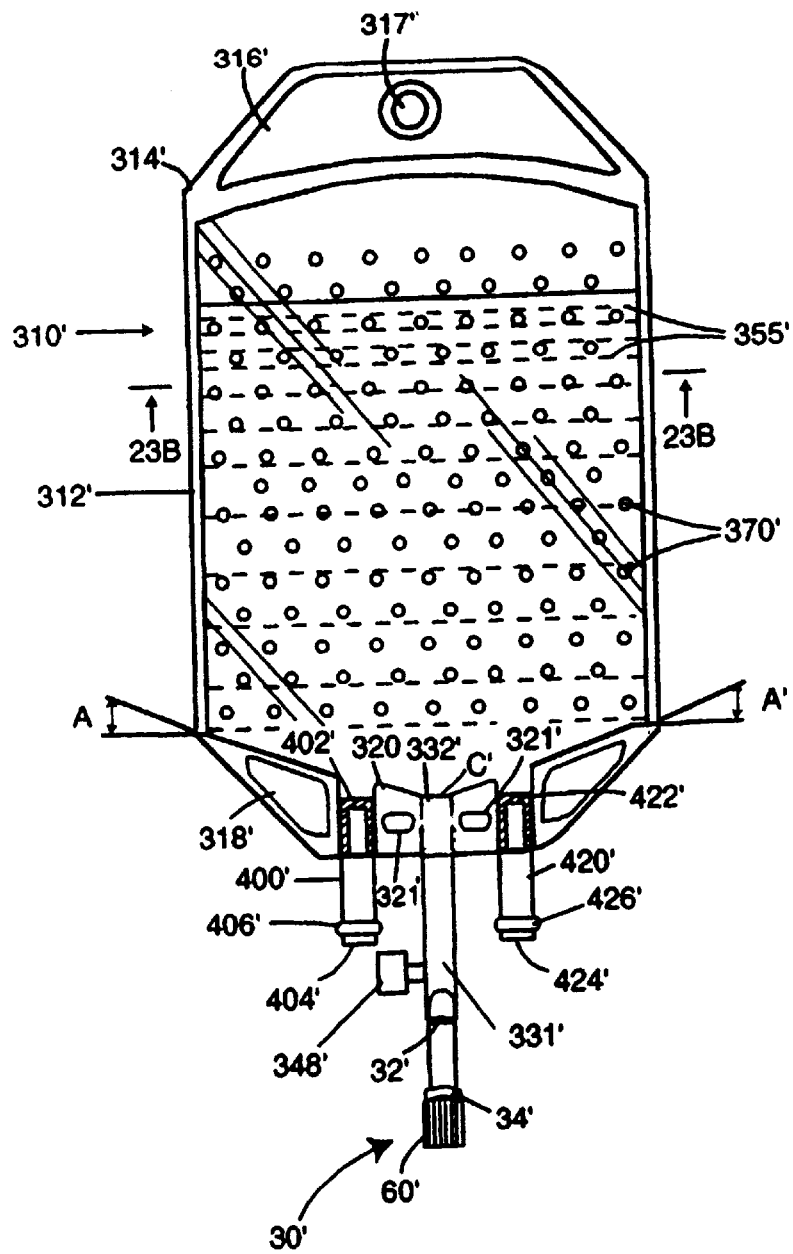
Figure 23B:
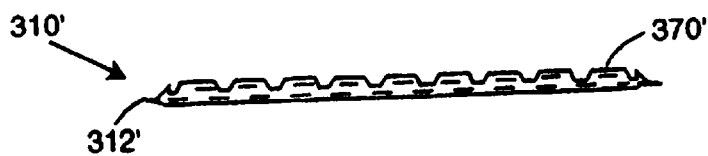
Figure 24A:
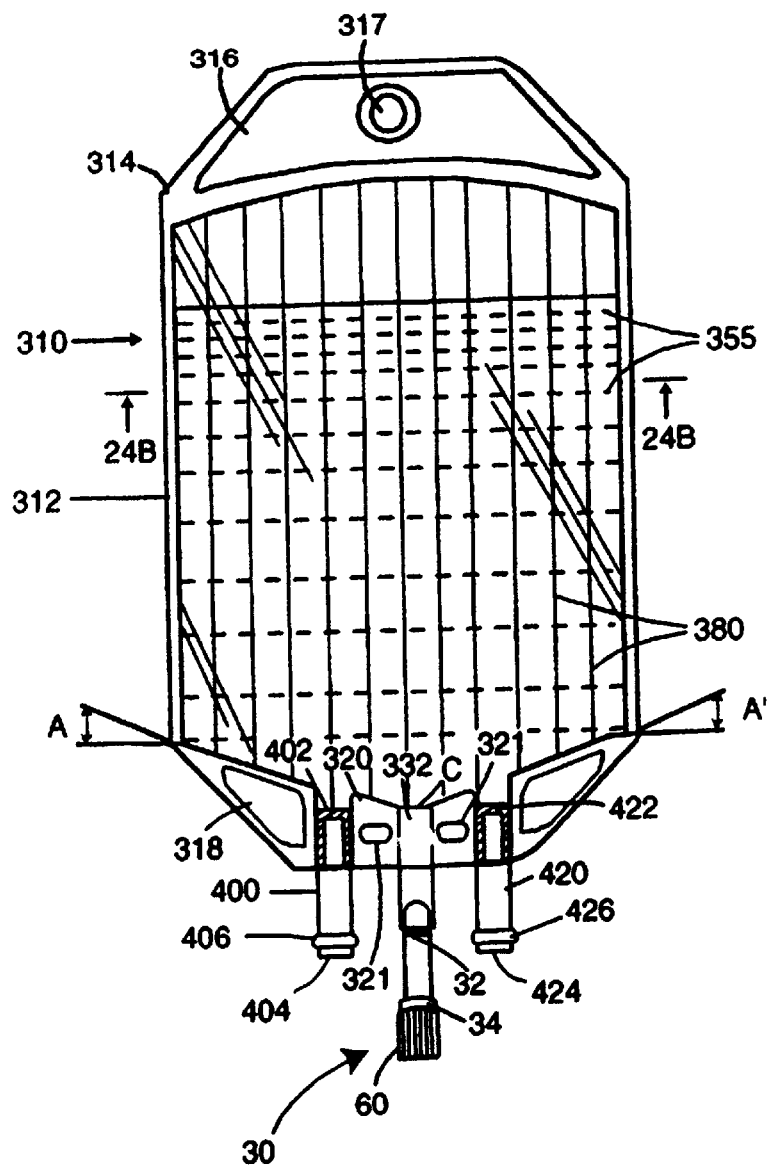
Figure 24B:
Figure 25A:
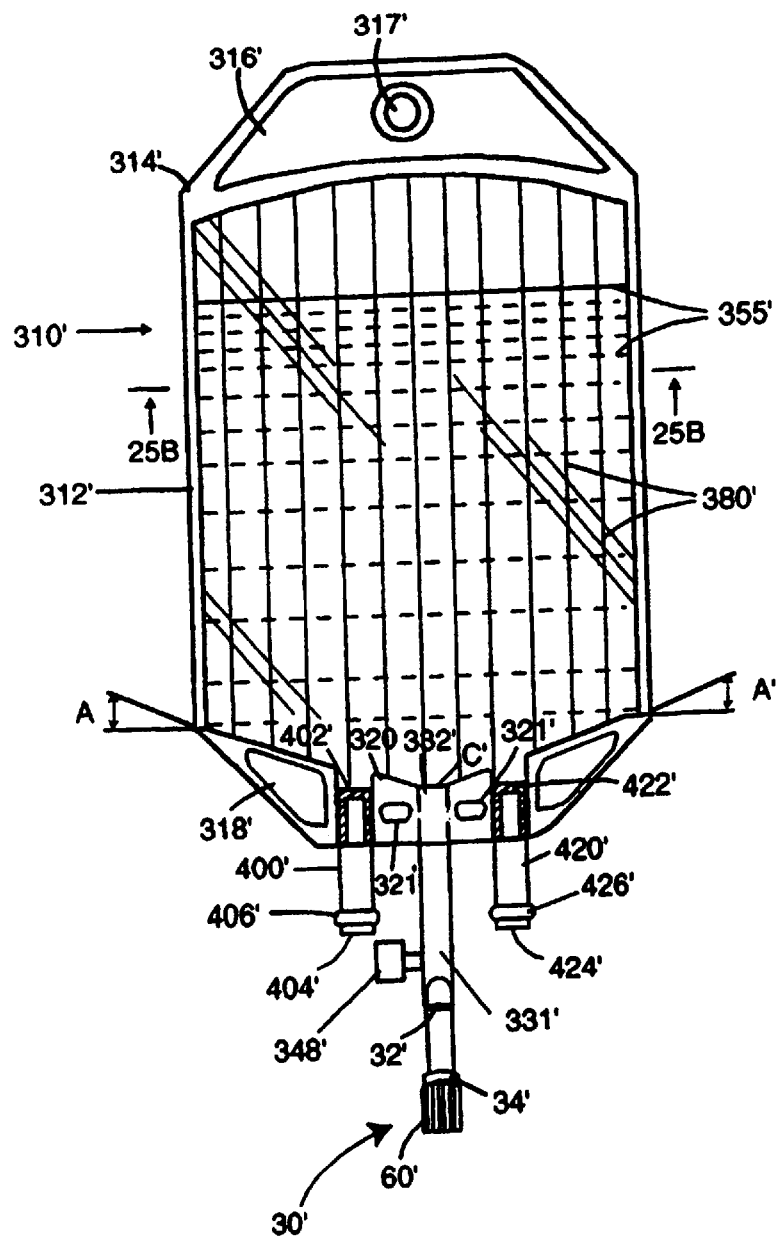
Figure 25B:
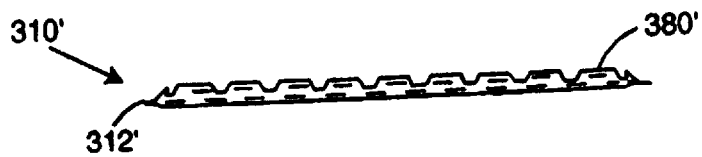
Figure 26A:
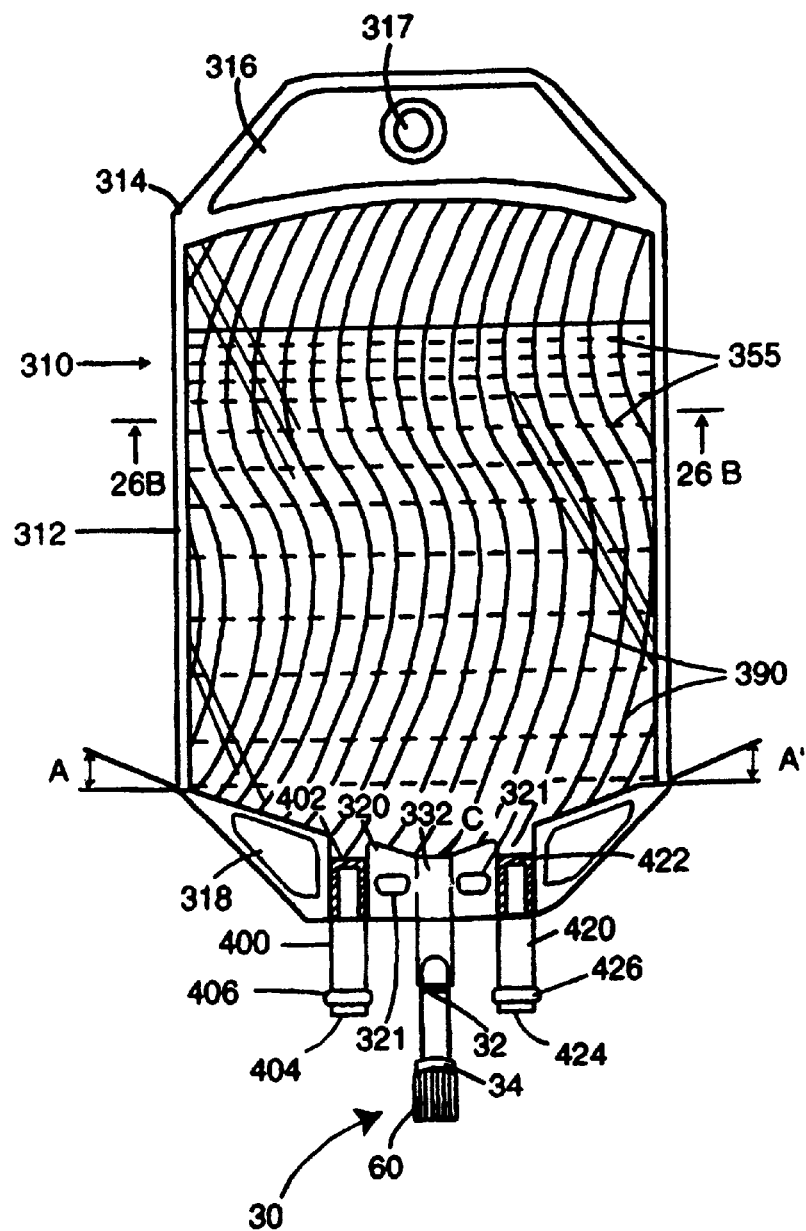
Figure 26B:
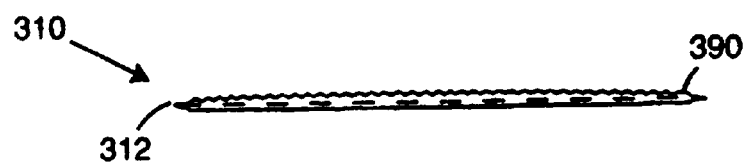
Figure 27A:
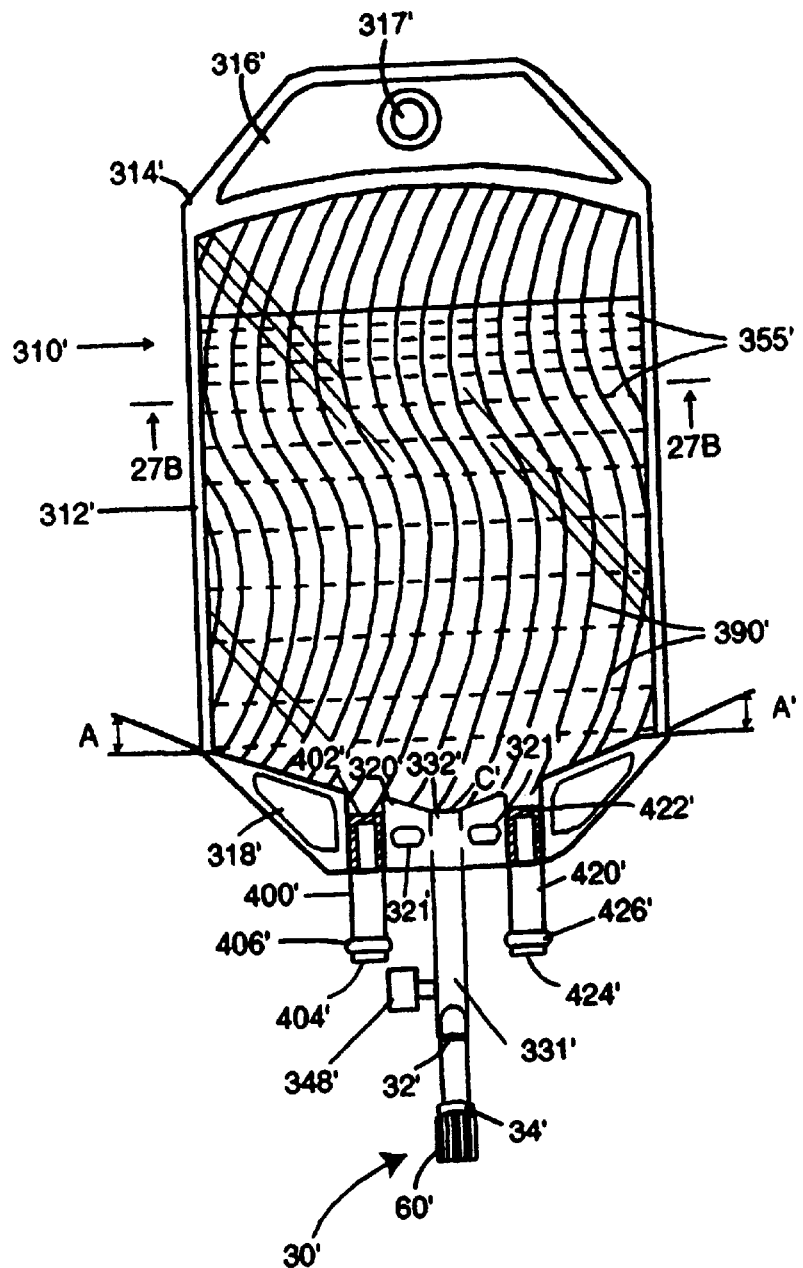
Figure 27B:
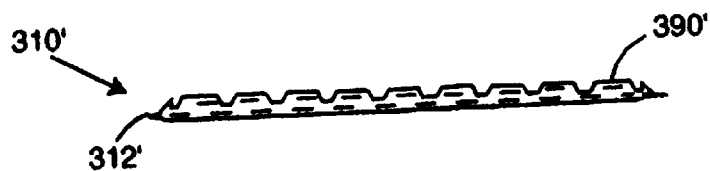

b) a needle access port located in the bottom portion of the pouch on one side of the IV access port; and c) a spike access port located in the bottom portion of the pouch on the other side of the IV access port;

FIG. 20A is a plan view of the universal, flexible container shown in FIG. 18 one wall of which is embossed in a checkerboard fashion;

FIG. 20B is a cross-section of the universal, flexible container shown in FIG. 20A taken along the line 20B—20B;

FIG. 21A is a plan view of the universal, flexible container shown in FIG. 19 one wall of which is embossed in a checkerboard fashion;

FIG. 21B is a cross-section of the universal, flexible container shown in FIG. 21A taken along the line 21B—21B; FIG. 22A is a plan view of the universal, flexible container shown in FIG. 18 one wall of which is embossed in a dotted fashion;

FIG. 22B is a cross-section of the universal, flexible container shown in FIG. 22A taken along the line 22B—22B;

FIG. 23A is a plan view of the universal, flexible container shown in FIG. 19 one wall of which is embossed in a dotted fashion;

FIG. 23B is a cross-section of the universal, flexible container shown in FIG. 23A taken along the line 23B—23B;

FIG. 24A is a plan view of the universal, flexible container shown in FIG. 18 one wall of which is embossed with vertically oriented channels;

FIG. 24B is a cross-section of the universal, flexible container shown in FIG. 24A taken along the line 24B—24B;

FIG. 25A is a plan view of the universal, flexible container shown in FIG. 19 one wall of which is embossed with vertically oriented channels;

FIG. 25B is a cross-section of the universal, flexible container shown in FIG. 25A taken along the line 25B—25B;

FIG. 26A is a plan view of the flexible container shown in FIG. 19 one wall of which is embossed with vertically oriented S-shape channels;

FIG. 26B is a cross-section of the universal, flexible container shown in FIG. 26A taken along the line 26B—26B;

FIG. 27A is a plan view of the universal, flexible container shown in FIG. 19 one wall of which is embossed with vertically oriented S-shape channels; and FIG. 27B is a cross-section of the universal, flexible container shown in FIG. 27A taken along the line 27B—27B.

DETAILED DESCRIPTION OF THE INVENTION

Referring to FIGS. 1, 2A, 2B, 2C and 2D, there is shown an intravenous bag 10 of conventional generally rectangular configuration made of inert, flexible, polymeric material, such as polyvinylchloride. The single use universal connector of the present invention will be described in reference to such flexible, polymeric bags, however, the single use universal connector can be used with other fluid containers such as bottles and vials of various configurations made of rigid or semi-rigid materials. Such containers will have fluid exit ports into which the universal connector can slideably be attached or it can be an integral part thereof. The IV bag 10 contains a medical fluid 12 therein, such as a therapeutic, diagnostic or nutritional preparation. The medical fluid 12 may be pre-sterilized in bulk prior to its transfer to the IV bag, or it may be sterilized in the IV bag using sterilizing equipment and techniques known in the art. The IV bag further comprises a fluid exit port or tube 14 the distal end 16 of which is in communication with medical fluid 12 and the proximal end 18 of which is to slideably receive distal end 32 of universal connector 30. Alternatively, universal connector 30 may be integral with fluid exit port or tube 14 of IV bag 10. In both cases, fluid exit port or tube 14 is sealed into IV bag 10 by bottom seam 20 of IV bag 10. On the proximal end 34 of single use universal connector 30, cap 60 is mounted having internal thread means thereon for enclosing said proximal end 34. Prior to use, cap 60 is removed from universal connector 30 for engagement with a female luer connector.

FIG. 2A shows the single use universal connector without the cap; FIG. 2B shows the universal connector with the cap; and FIG. 2C shows the cap, all views being shows in perspective.

Figure 3A:
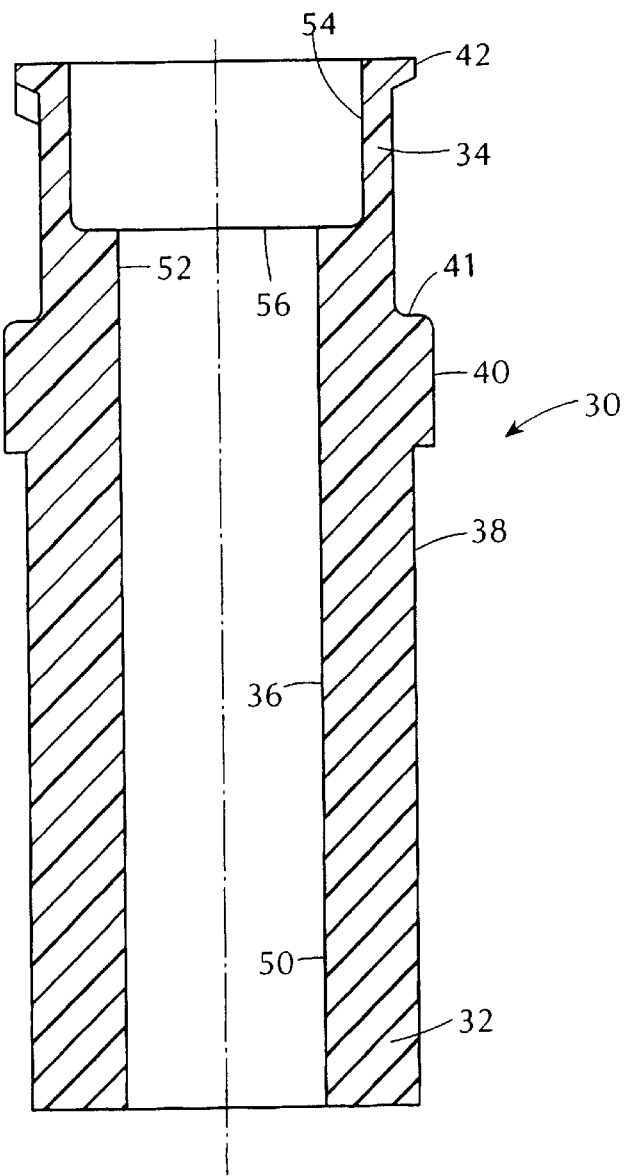
FIG. 3A is a cross-section of the universal connector without the cap attached taken along the line 3A—3A of FIG. 2A.
Figure 3A:
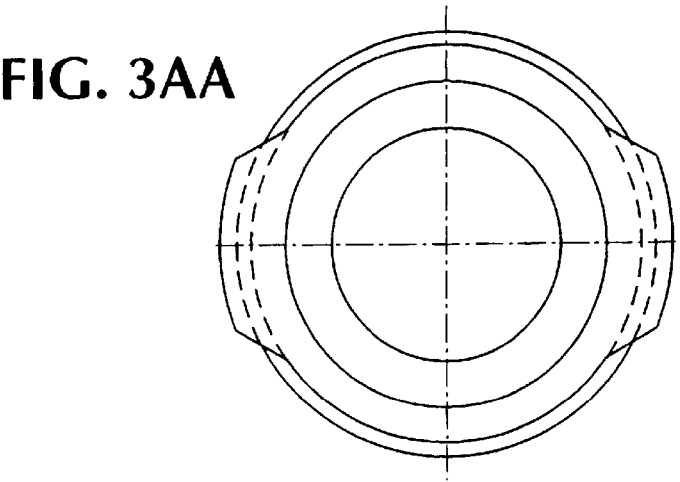
Figure 3B:
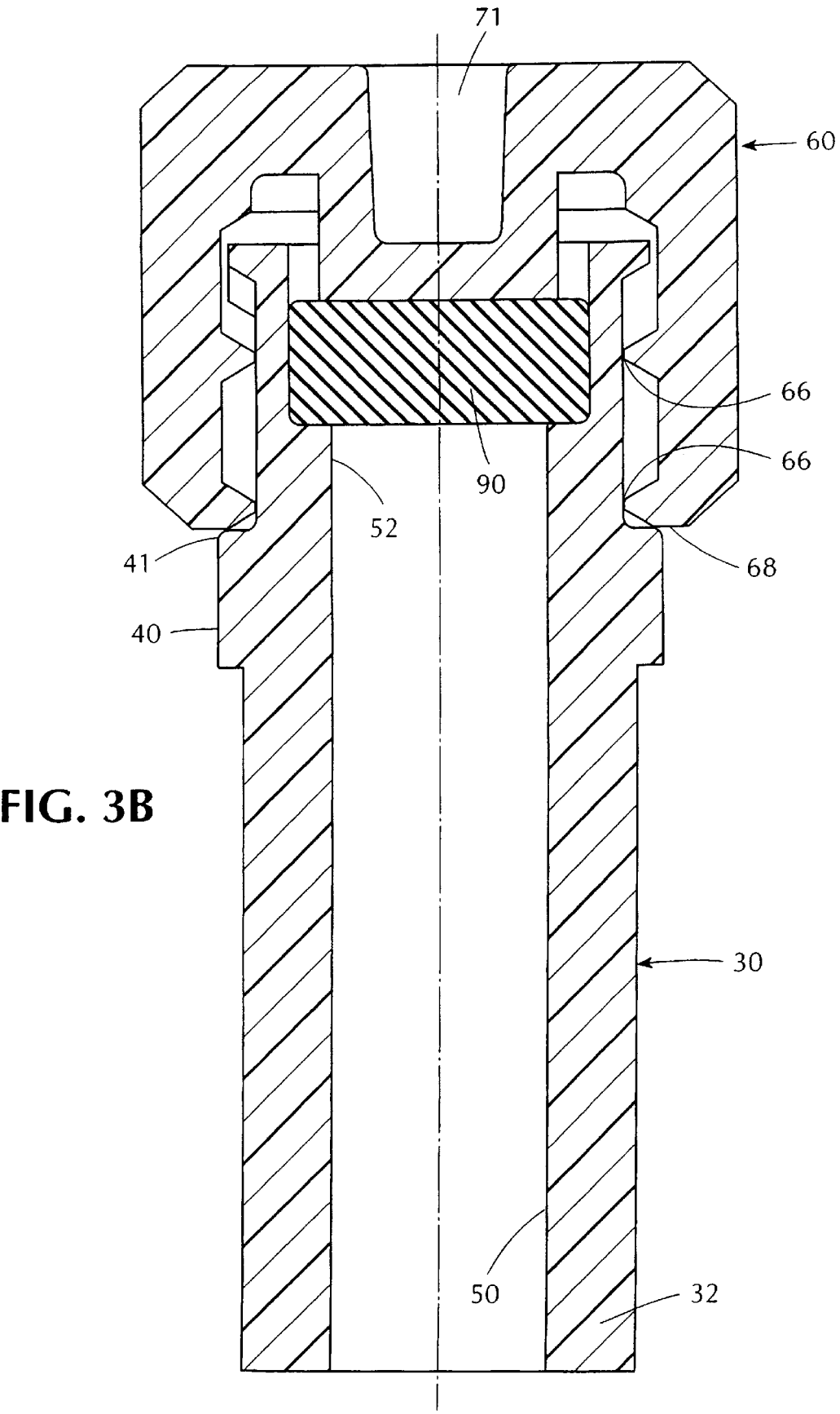
FIG. 3B is a cross-section of the universal connector with the cap attached taken along the line 3B—3B of FIG. 2B.
Figure 3C:
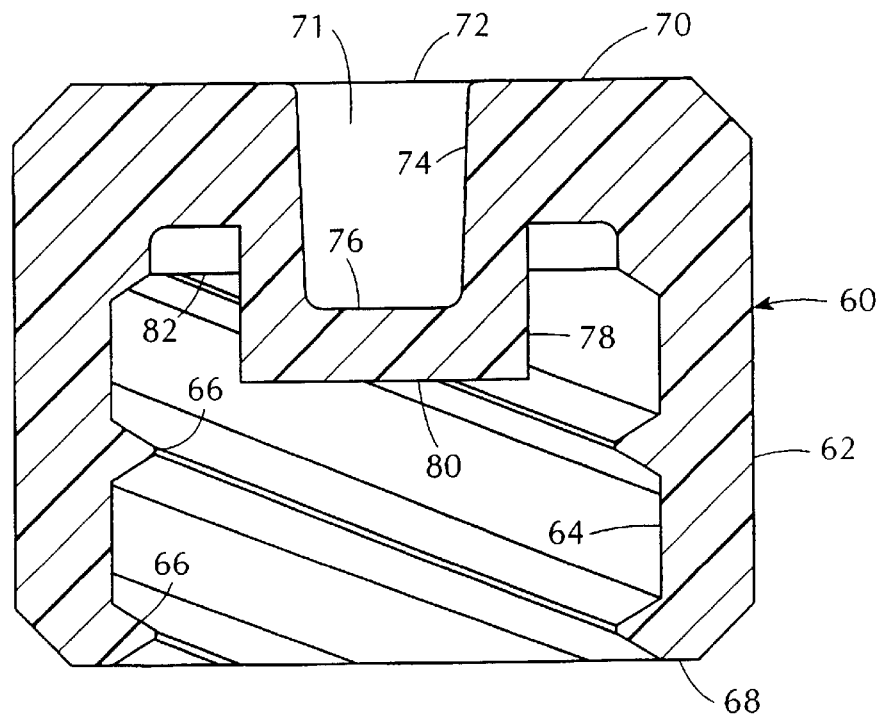
FIG. 3C is a cross-section of the cap taken along the line 3D—3D of FIG. 2D.
Figure 3C:
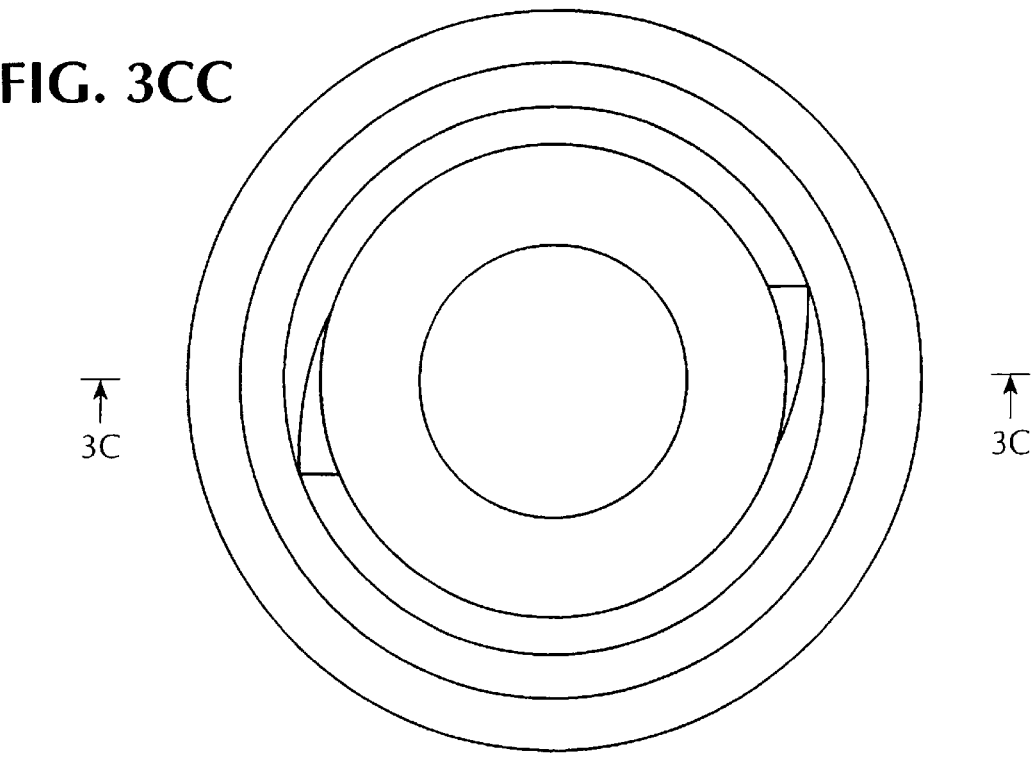

Reference is now being made to FIGS. 3A, 3AA, 3B, 3C and 3CC:

FIG. 3A shows a cross-sectional view of the universal connector without the cap taken along the line 3A—3A of FIG. 2A, and FIG. 3AA shows the top plan view thereof;

FIG. 3C shows a cross-section of the cap taken along the line 3D—3D of FIG. 2D, and FIG. 3CC shows the top plan view thereof; and FIG. 3B shows the single use universal connector assembly taken along the line 3B—3B of FIG. 2B.

Universal connector 30 is of tube-like configuration comprising: distal end 32 and proximal end 34; inside wall 36 and outside wall 38. Integral part of outside wall 38 at the proximal end 34 thereof is positioned first cap-locking ring 40 spaced from second cap-locking ring 42. First cap-locking ring serves as a male thread to receive cap 60 and to engage its internal threads 66 and 66'. Second cap-locking ring 40 having proximal end 41 has a larger external diameter than the distance defined by a line connecting internal threads 66–66' located at the proximal end 68 of cap 60. Second cap locking-ring 42 serves as stopping means for cap 60 when cap 60 is threaded onto universal connector 30.

Inside wall 36 of single use universal connector 30 comprises: a distal end 50 and proximal end 52. Distal end 50 is designed to slideably and sealingly engage fluid exit port or tube 14 to slide into the fluid exit port through its proximal end 18.

At the proximal end 52 of single use universal connector 30 a cylindrical opening is defined by side wall 54 and bottom wall 56. The cylindrical opening is designed to receive cylindrical protuberance defined by outside walls 78 and 80 of cap 60.

Bottom wall 56 of cylindrical opening in single use universal connector 30, as best can be seen in FIG. 3B, comprises a rubber or other elastomeric membrane 90 bonded to the universal connector. The elastomeric membrane is of cylindrical configuration and seals the fluid channel defined by the proximal end of inside wall 52 of universal connector 30. The membrane is of inert gas-impermeable polymeric material capable of flexing under internal or external pressures such as exerted during steam sterilization. Preferably the membrane has a thickness of from about 0.001 mm to about 1.00 mm and a durometer of from about 25 to about 80 Shore A. Suitable elastomeric materials for constructing the membrane include:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

As best can be seen in FIGS. 3C and 3CC, cap 60 is designed for securely closing single use universal connector 30 at the proximal end 34 thereof, and protecting elastomeric membrane 90 from contact with the outside environment. The configuration of the cap closely approximates the female luer connector shown in FIG. 7 which, in addition to the features detailed as the description of the cap proceeds, also contain a tubing conduit which is part of the female luer connector. FIGS. 3C and 3CC show cylindrical cap 60 comprising: outside wall 62 and inside wall 64. Outside wall 62 comprises: bottom wall 68; top wall 70; and central portion 72 of top wall 70. Inside wall 64 comprises: internal threads 66 and 66' extending towards the center of the cap; a cylindrical protuberance defined by outside wall 78 and bottom wall 80 extending distally into the space defined by the inside wall; and shoulder portion 82 connecting inside wall 64 and outside wall 78 of the cylindrical protuberance. In the proximal end of cap 60 there is located plug 71 defined by central portion 72 of top wall 70, and bottom wall 76. Plug 71 may be integral with the cap such as obtained by blow molding technique or, as shown in FIGS. 3C and 3CC, the plug may be manufactured separately and subsequently sealed into the cap.

Referring again to FIGS. 3A, 3B and 3C, when cap 60 is threaded onto single use universal connector 30, bottom wall of protuberance 80 will be spaced from elastomeric membrane 90 allowing the membrane to flex outward under pressure, such as created during heat sterilization. However, spacing should not be more than about 2 to 3 mm so that under accidentally high pressures, bursting of the membrane is prevented by the support of bottom wall 80 of cylindrical protuberance.

Figure 4:
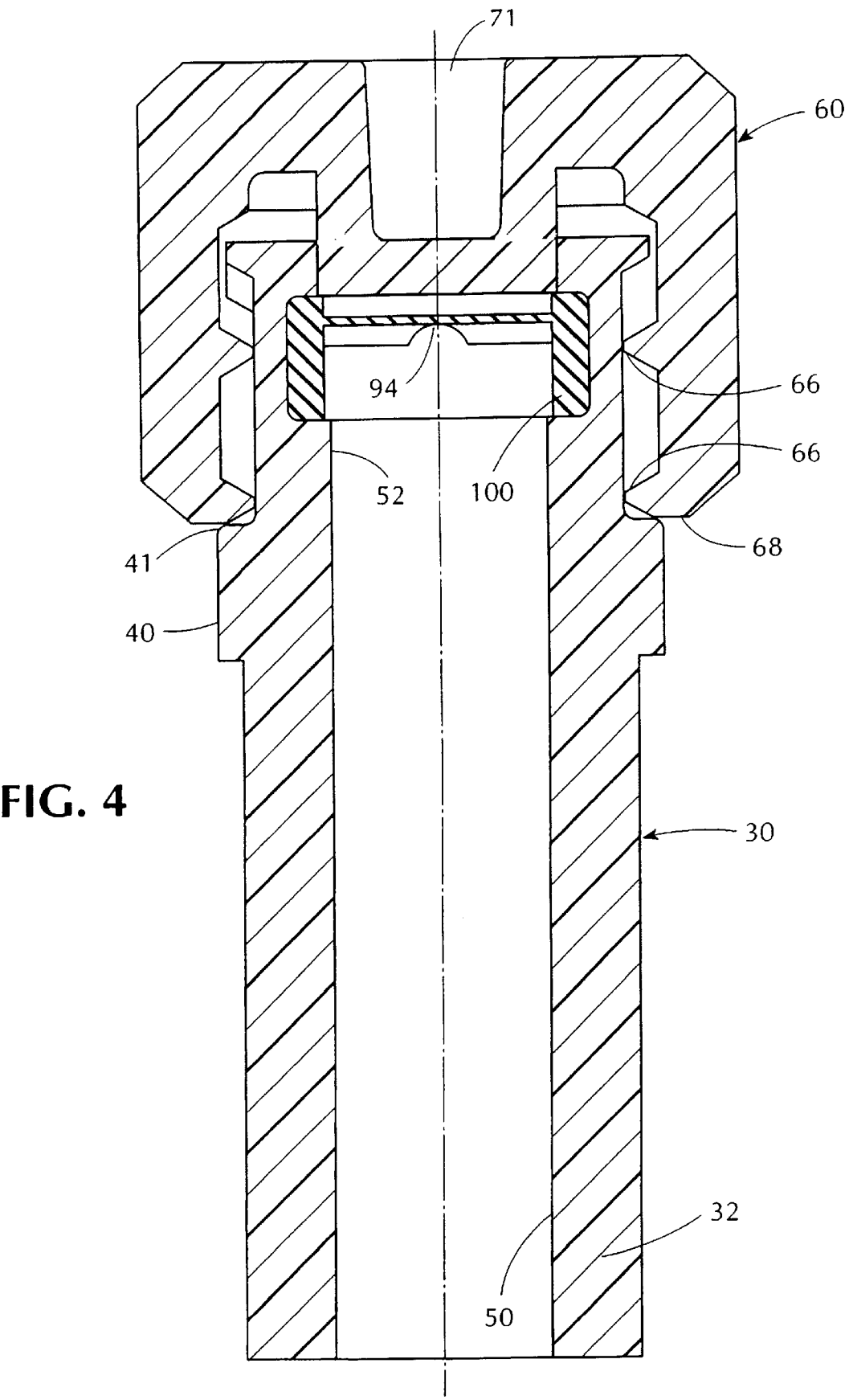
Figure 4A:
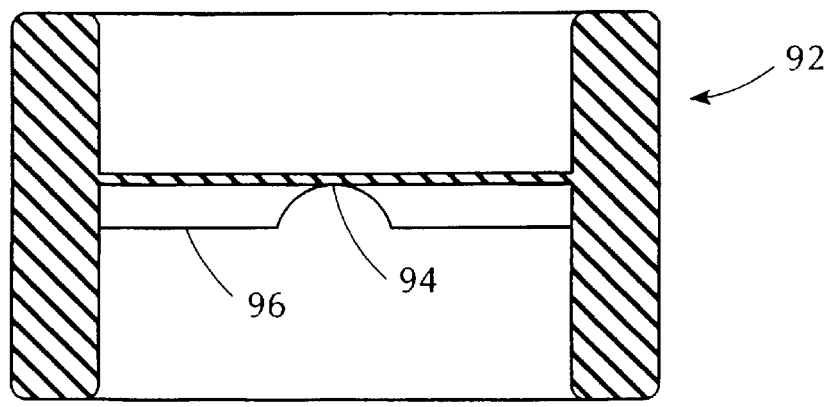
FIG. 4A is the rubber seal shown in cross-sectional view in FIG. 4 removed from the universal connector.
Figure 4B:
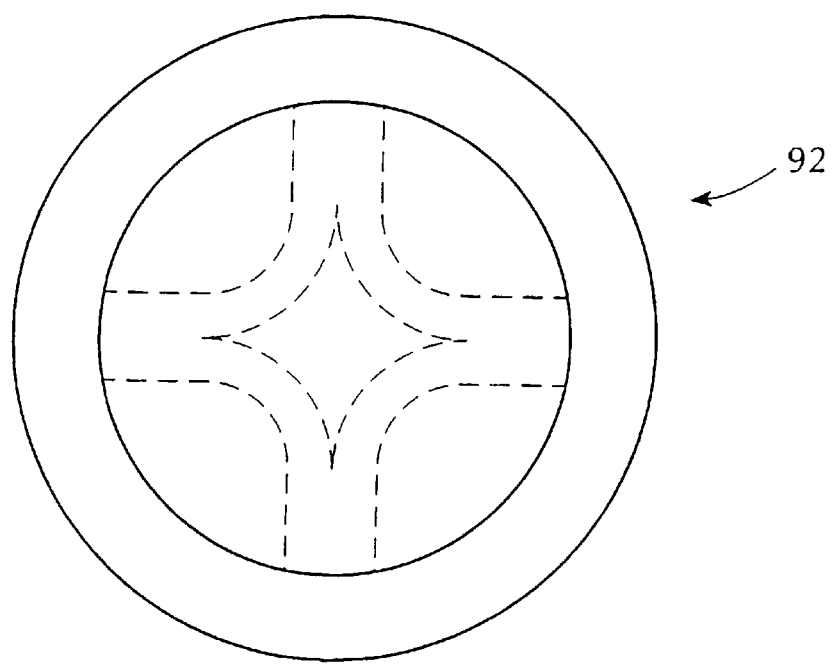
FIG. 4B is the top plan view of the rubber seal shown in cross-sectional view in FIG. 4A.

FIGS. 4, 4A and 4B show another embodiment of the single use universal connector of the present invention in cross-sectional view assembled with the cap wherein like numbers denote the same parts as in FIGS. 3A, 3AA, 3B, 3C and 3CC. The figures show a different elastomeric membrane having a generally dome-shaped configuration in the center thereof. Elastomeric membrane 92, shown in cross-section, is of cylindrical configuration and is bonded to single use universal connector 30. Preferably, the membrane has a thickness of from about 0.001 mm to about 1.00 mm and a durometer of from about 25 to about 80 Shore A. Suitable elastomeric materials constructing the membrane include those described for the embodiment described in the embodiment shown in FIGS. 3A, 3AA, 3B, 3C and 3CC. The dome-shape configuration 94 rises above the horizontal portion 96 of elastomeric membrane 92 towards the distal end of single use universal connector 30 and has the same thickness as the horizontal portion 96 thereof. The dome-shape configuration allows easy rupture of the membrane at 94 when female luer connector is threaded into single use universal connector 30 in order to establish fluid communication.

Figure 5:
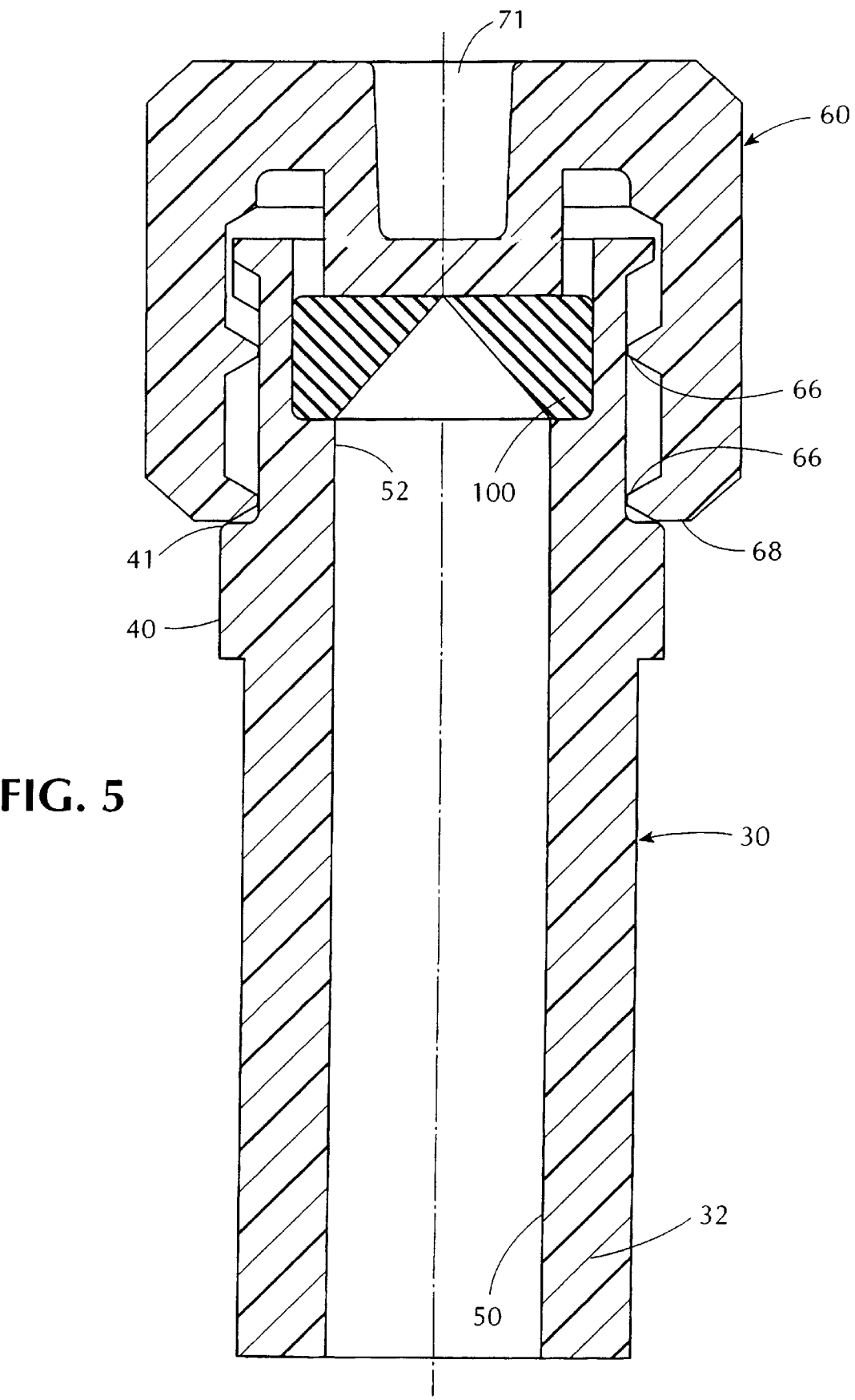
Figure 5A:
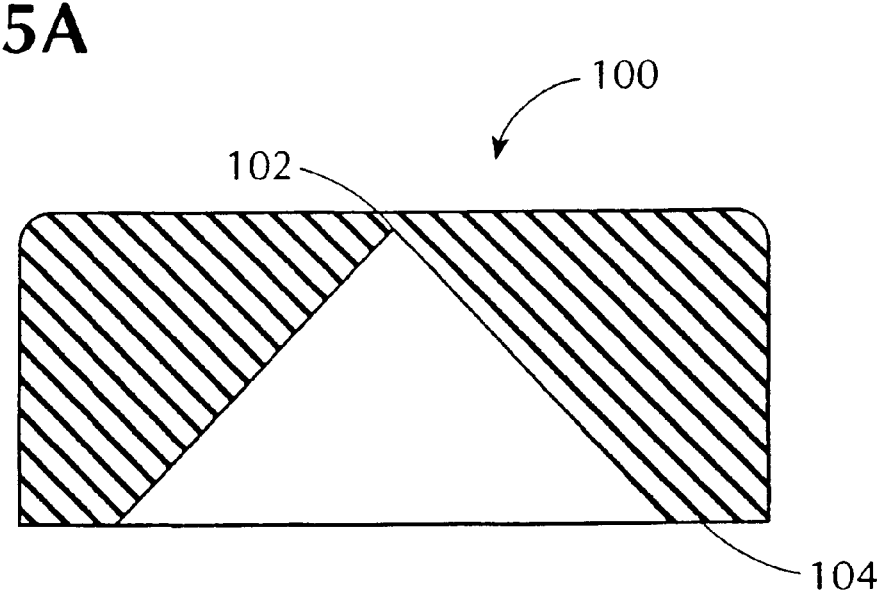
FIG. 5A is the rubber seal shown in cross-sectional view of FIG. 5 removed from the universal connector.
Figure 5B:
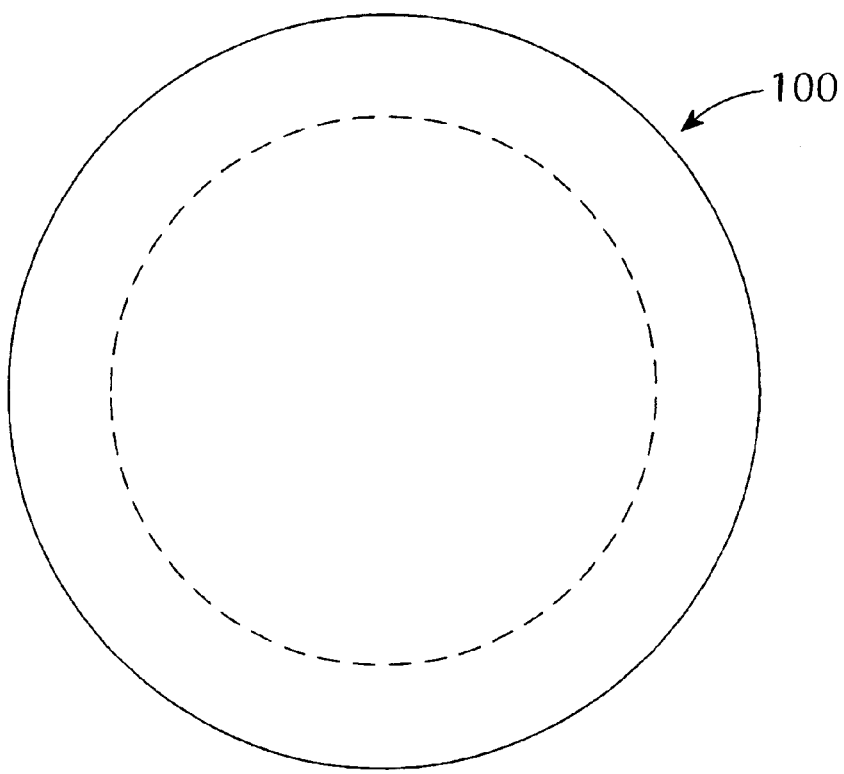
FIG. 5B is a top plan view of the rubber seal shown in cross-sectional view in FIG. 5A.

FIGS. 5, 5A and 5B show still another embodiment of the single use universal connector of the present invention in cross-sectional view assembled with the cap attached wherein like numbers denote the same parts as in FIGS. 3A, 3AA, 3B, 3C and 3CC. The figures show an elastomeric membrane 100 having a large generally cone-shaped 102 configuration in the center thereof. The cone-shape configuration having a tip which rises above the horizontal portion 104 of elastomeric membrane 100 toward the distal end of the single use universal connector 30 and has from about 5% to about 20% of the thickness of the elastomeric membrane 100. The cone-shape configuration allows easy rupture of the membrane at 102 when female luer connector is threaded into single use universal connector 30 in order to establish fluid communication.

Figure 6:
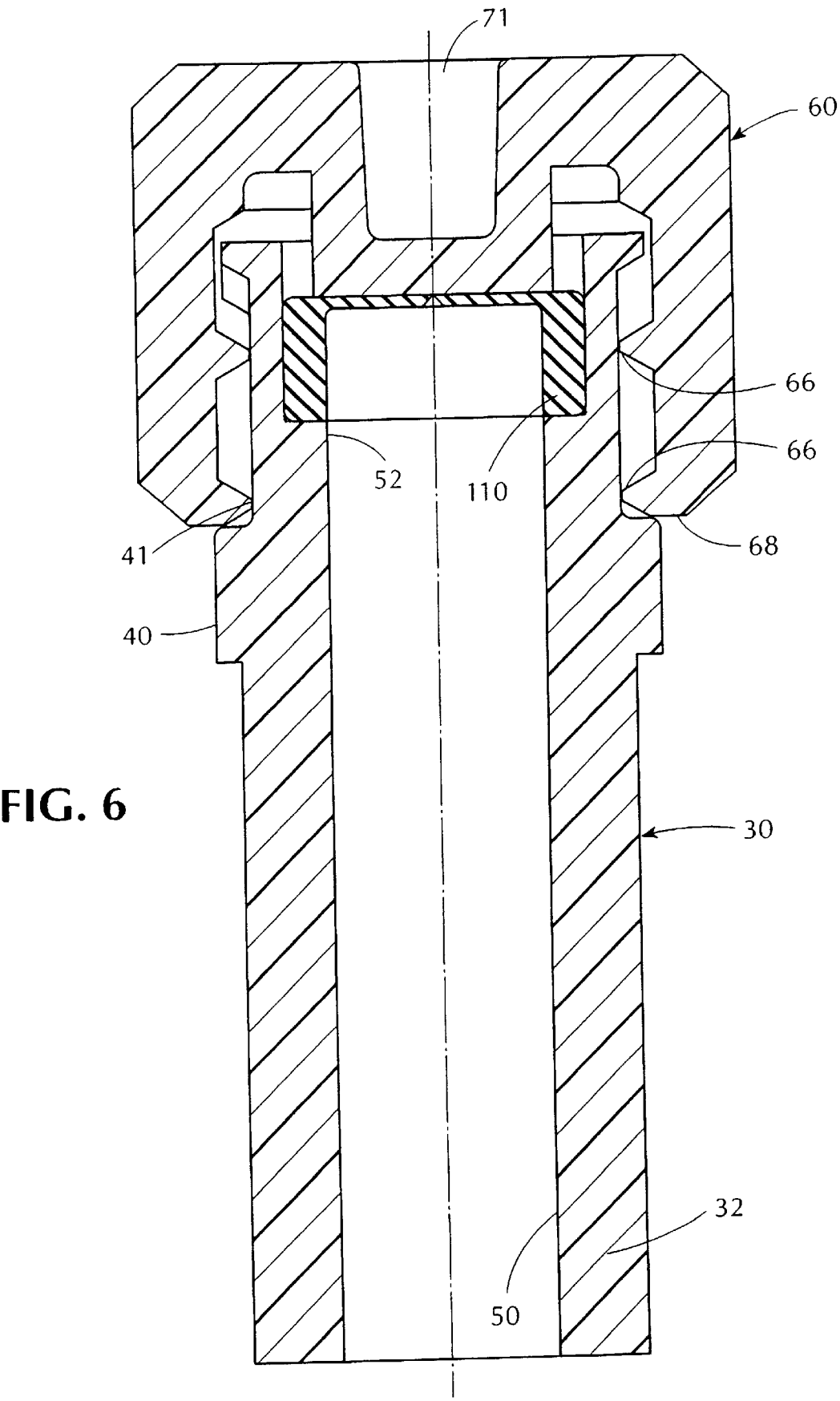
Figure 6A:
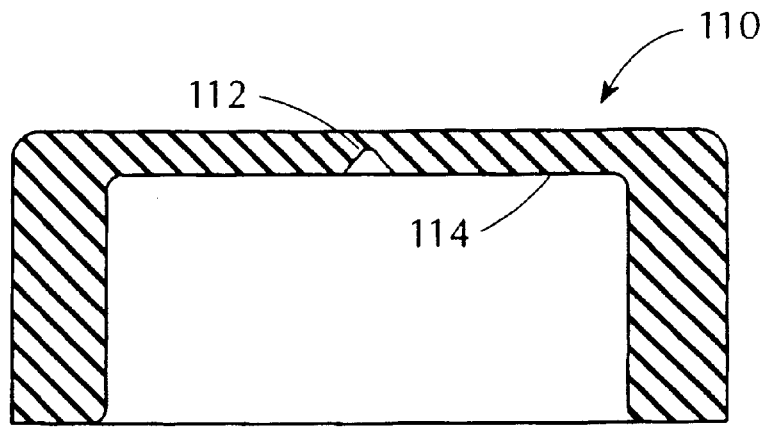
FIG. 6A is the rubber seal shown in cross-sectional view in FIG. 6 removed from the universal connector.
Figure 6B:
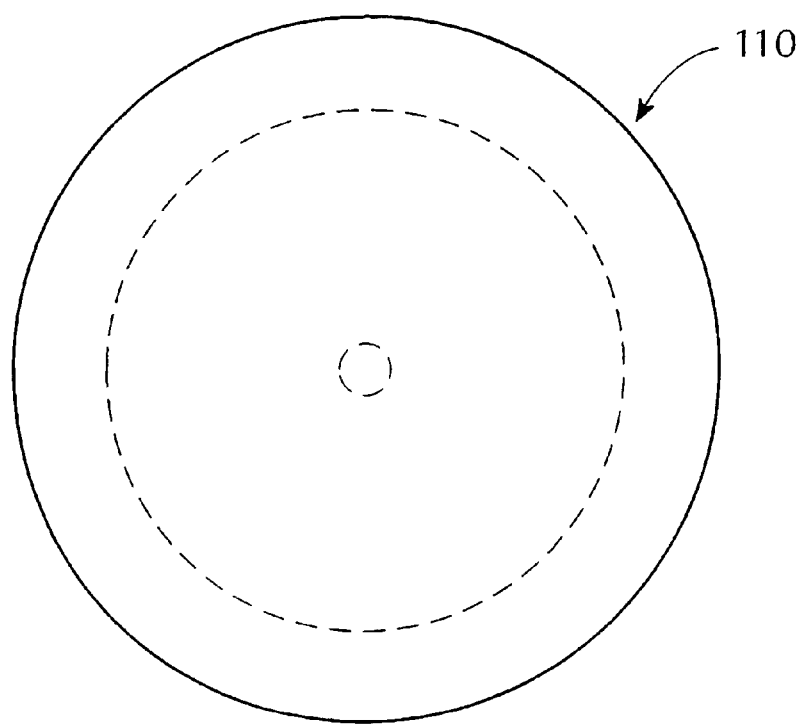
FIG. 6B is a top plan view of the rubber seal shown in c ross-sectional view in FIG. 6A.

FIGS. 6, 6A and 6B show still another embodiment of the single use universal connector of the present invention in cross-sectional view assembled with the cap wherein like numbers denote the same parts as in FIGS. 3A, 3AA, 3B, 3C and 3CC. The figures show an elastomeric membrane 110 having a conic section configuration 112 in the center thereof which rises above the horizontal portion 114 of elastomeric membrane 110 towards the distal end of universal connector 30. The thickness of the elastomeric membrane above the conic section is of from about 10% to about 60% of the thickness of the horizontal portion 114 of elastomeric membrane 110. The conic section configuration allows easy rupture of the membrane at 112 when female luer connector is threaded into single use universal connector 30 in order to establish fluid communication.

Figure 7:
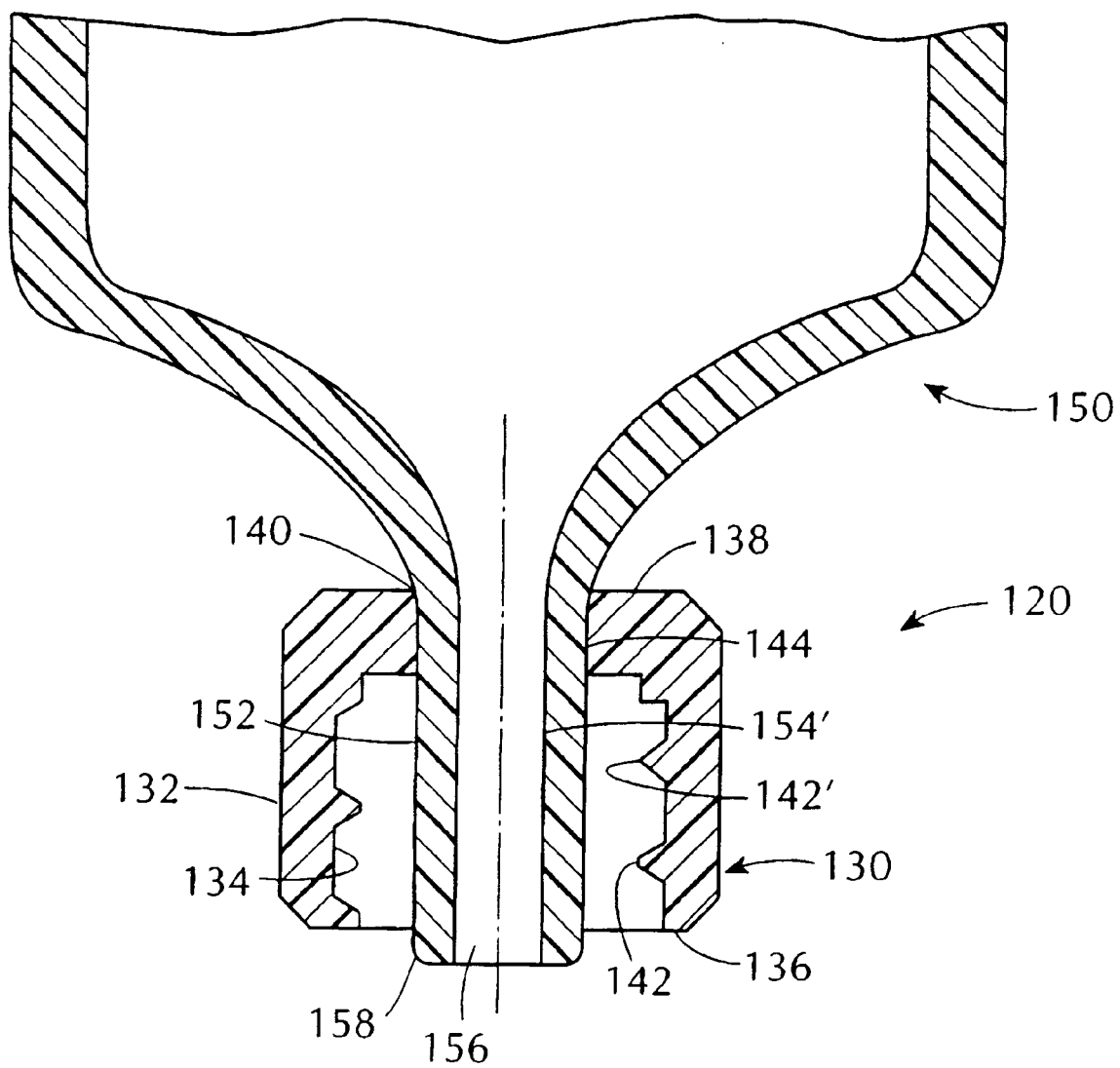

FIG. 7 shows in cross-sectional view a female luer connector attachable to each of the embodiments of the present invention. The female luer connector 120 comprises a cylindrical cap 130 and tubing conduit 150. Cylindrical cap 130 closely approximates cylindrical cap 60 of universal connector shown in FIGS. 3C and 3CC and its function is to be threaded onto universal connector when fluid communication is desired. Prior to threading cylindrical cap 130 of female luer connector 120 onto universal connector 30, cylindrical cap 60 is removed and then replaced by cylindrical cap 130 of female luer-connector 120.

Cylindrical cap 130 of female luer connector 120 comprises outside wall 132 and inside wall 134. Outside wall 132 comprises: bottom wall portion 136; top wall portion 138; and central portion 140 of top wall portion 138. Inside wall 134 comprises: internal threads 142 and 142' extending towards the center of the cap.

Tubing conduit 150 is positioned in cylindrical cap 130 of female luer connector 120 at its top central portion 140. Thickened outside wall portion 144 parallelly faces outside wall 152 of tubing conduit 150 and is permanently attached thereto by adhesive or other suitable means known in the art. Tubing conduit further comprises: inside walls of tubing conduit 154 and 154' forming a fluid channel 156; and bottom end portion of tubing conduit 158 which extends beyond bottom portion 136 of cylindrical cap 60 of universal connector 30. When threaded onto universal connector 30, female luer connector 120 travels towards second cap-locking ring 42, contacts elastomeric membrane 90 or 92 or 100 or 110 with its bottom and portion 158 and exerts pressure thereon in a twisting motion. The exerted force ruptures the elastomeric membrane thereby allowing fluid communication between the female luer connector 120 and the content of the intravenous infusion bag.

The single use universal connector 30 may also be used in containers, such as bottles and vials the contents of which are intended to be accessed by a hypodermic syringe having either a sharp or blunt cannula. When fluid withdrawal or fluid addition is desired, cylindrical cap 60 of universal connector 30 is removed and the elastomeric membrane is pierced by the cannula providing access to the content of the container or withdrawal therefrom.

The single use universal connector used in conjunction with the first embodiment of the present invention is shown in FIGS. 8 to 17B.

Figure 8:
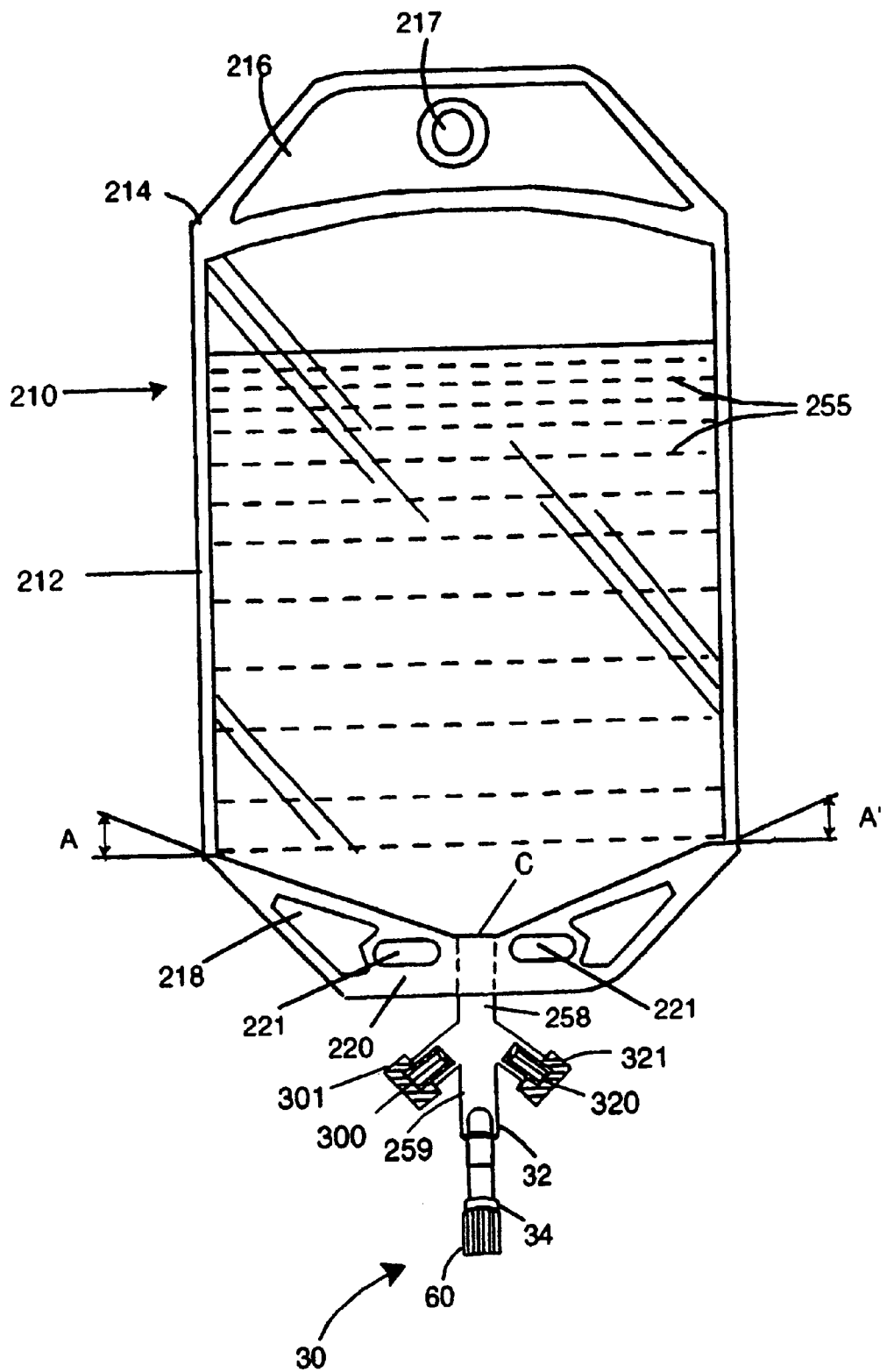
FIG. 8 is a plan view of a universal flexible container in accordance with the present invention showing:
 a) a pouch; and
 b) a combination access member of inverted Y shape configuration having a stem with proximal and distal ends and a pair of tines comprising:
  1) an IV access port at the distal end of the stem equipped with the single use universal connector;
  2) a needle access port located in one of the tines of the combination access member; and
  3) a spike access port located in the other of the tines of the combination access member.
Figure 9:
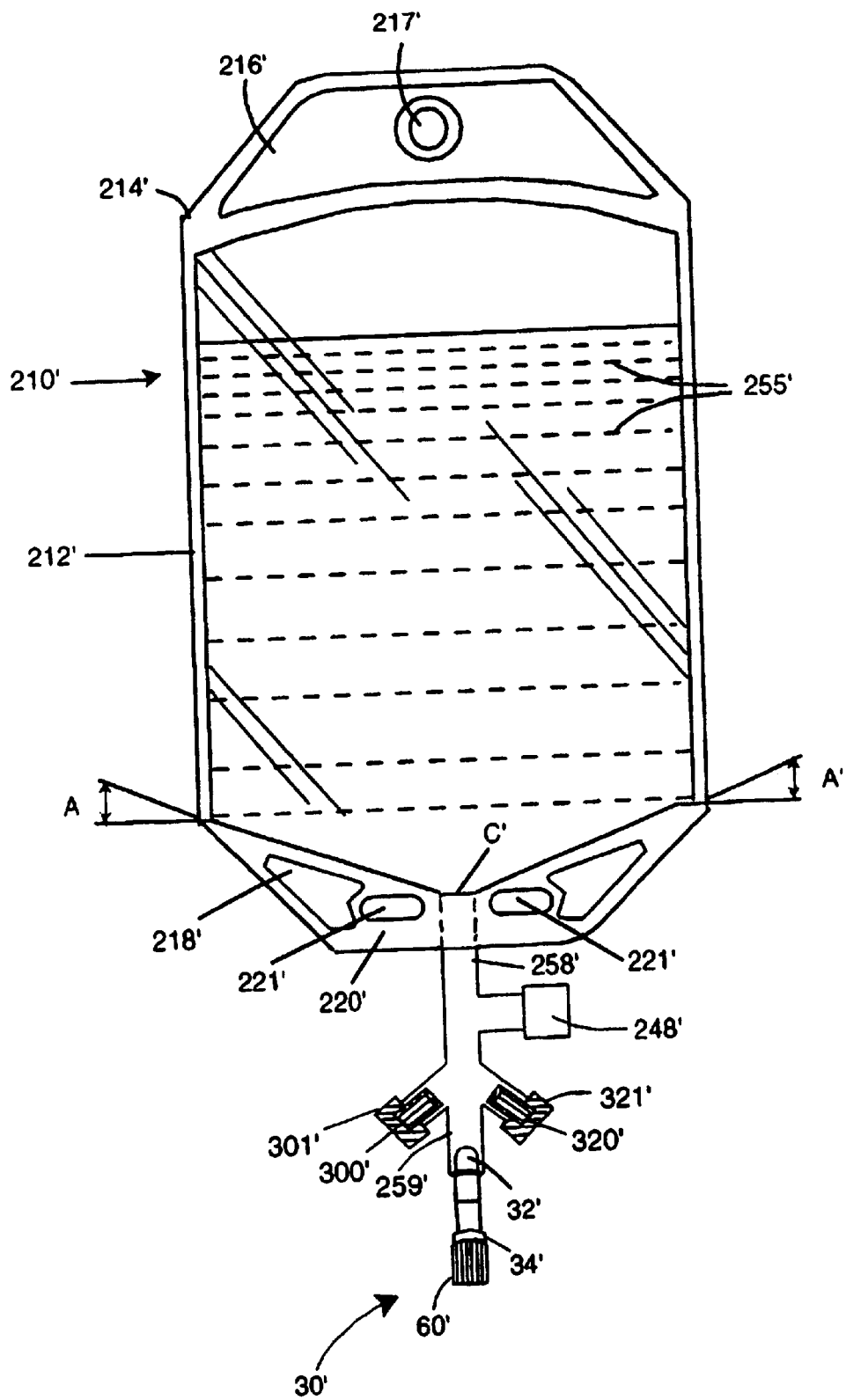
FIG. 9 is a plan view of another embodiment of the present invention showing:
 a) a pouch; and
 b) a combination access member of inverted Y shape configuration having a stem with proximal and distal ends and a pair of tines comprising:
  1) an IV access port at the distal end of the stem equipped with the single use universal connector;
  2) a vent at the proximal end of the stem;
  3) a needle access port located in one of the tines of the combination access member; and
  4) a spike access member located in the other of the tines of the combination access member.

In the drawings where like numerals indicate like elements or portions, the reference characters 210 and 210' in FIGS. 8 and 9 indicate the container which, in this preferred embodiment, is a pouch-like device, comprising two superimposed sheets of suitable length and width made of flexible or pliable materials, such as polymeric materials including polyethylene, polypropylene and preferably thermoplastic materials.

The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 255 in FIG. 8 and 255' in FIG. 9, it assumes the shape of a small cushion. The superimposed sheets are joined together along marginal areas 212, 212', 214, 214', 126, 216', 218, 218', 220 and 220' as shown in FIGS. 8 and 9 respectively.

The bottom portion of pouch 210 or 210' terminates in first angle A and second angle A' from the center C or C' of said bottom portion and relative to a horizontal plane crossing the center C or C' of said bottom portion to direct and facilitate the flow of content contained in the pouch towards a combination access member of inverted Y shape configuration 258 or 258'. Angles A and A' are of from about 5° to about 4520 , preferably from 10° to 30° and most preferably from 10 to 20 °.

Combination access member, having an inverted Y shape configuration is located at center C or C' of the bottom portion of pouch 210 or 210' comprising:

a steam having a proximal end 258 or 258' and a distal end 259 or 259'; and a pair of tines integral with the stem. The proximal end 258 or 258' is located at the bottom center portion of the pouch and below a horizontal plane crossing the center C or C' of said bottom portion so that all the liquid content of the pouch can be drained from the pouch into the stem. The proximal end 258 or 258' is sealed between the two superimposed sheets in the periphery thereof which form the pouch.

A pair of tines extend from and are integral with the stem forming the inverted Y shape of the combination access member. One of the tines constitute the needle access port 300 or 300' and is covered by cap 301 or 301'. The other of the tines constitute the spike access port 320 or 320' and is covered by cap 321 or 321'. The cap covering the needle and spike access ports maintain sterility of content of the pouch until the point of use.

Referring to FIG. 8, the stem of the combination access member is attached at its distal end 259 to single use universal connector 30 which comprises: a distal end 32, proximal end 34 and cap 60.

FIG. 9 shows another variation of the first embodiment of the present invention in which the pouch 210' is the same as the pouch 210 shown in FIG. 8, however, the combination access member includes a vent 248' positioned at the proximal end 258' of the stem.

Referring to FIGS. 8 and 9, access to needle access port 300 or 300' using a steel needle is gained by removing caps 301 or 301'. Access to spike access port 320 or 320' using a plastic spike is gained by removing caps 321 or 321'.

Marginal areas 216 and 216' in FIGS. 8 and 9 preferably comprise at least one hole 217 or 217' for suspending the pouch when it is in use for delivering the content of the pouch to a delivery site.

Marginal areas 220 and 220' in FIGS. 8 and 9 preferably comprise at least one, and more preferably a plurality, of hole(s) 221 and 221' to facilitate suspending the pouch during the filling process.

The universal, flexible container of the present invention may be used for delivering a single dose or multi-dose of parenteral solution. The needle and spike ports, along with the IV access port, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was discovered that if the inside wall of the first sheet or the second sheet forming the pouch 210 of FIG. 8 or pouch 210' of FIG. 9 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Figure 10A:
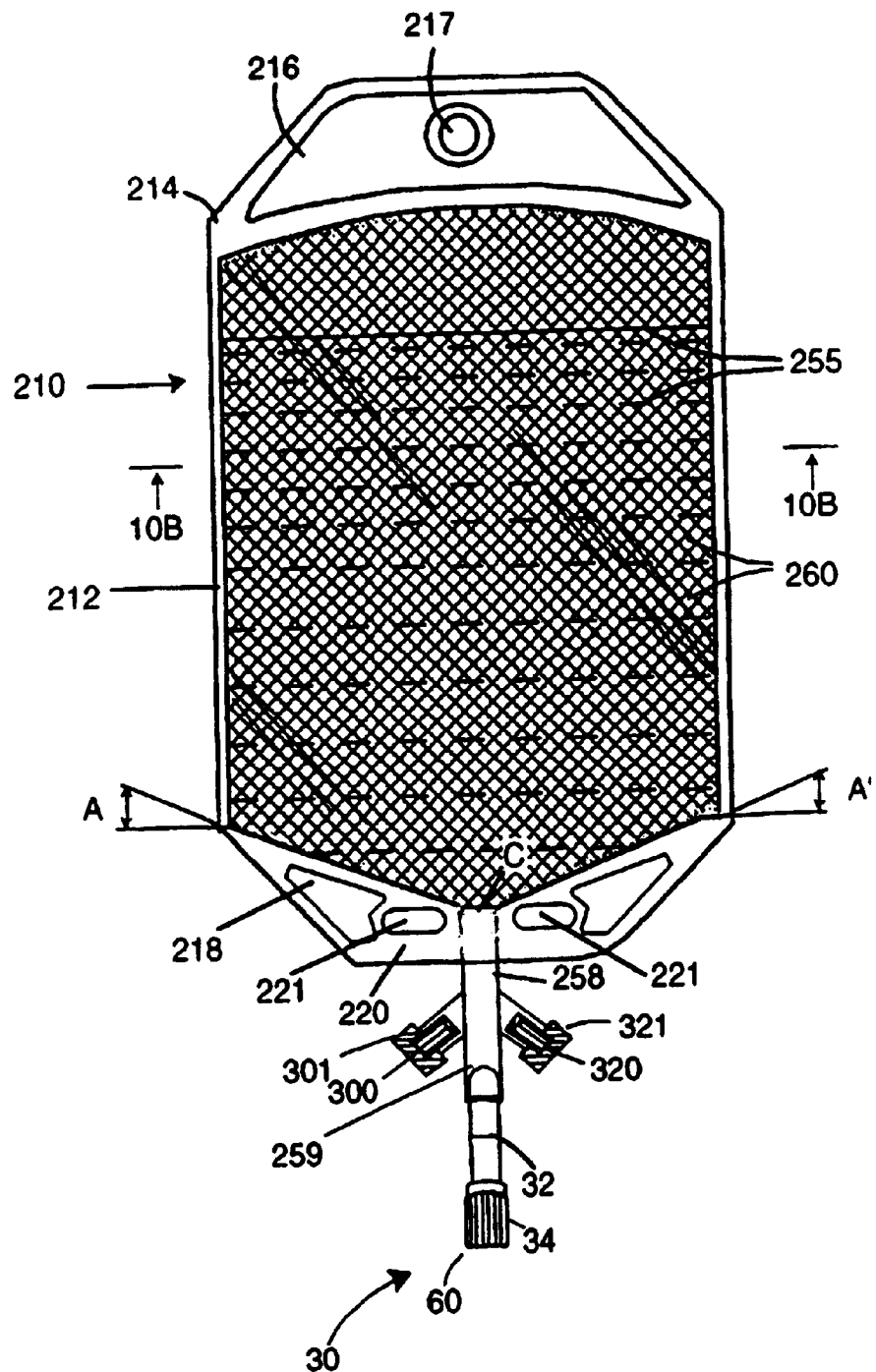
FIG. 10A is plan view of the universal, flexible container shown in FIG. 8 one wall of which is embossed in a checkerboard fashion.
Figure 10B:
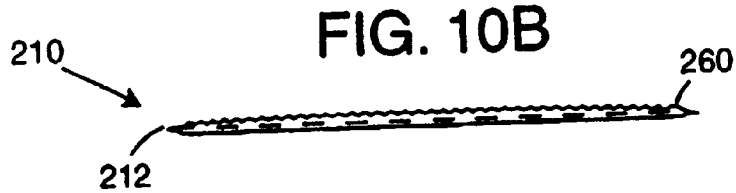
FIG. 10B is a cross-section of the universal, flexible container shown in FIG. 10A taken along the line 10B—10B.

Referring to FIG. 10A and FIG. 10B, the inside wall of first sheet of pouch 210 shown in FIG. 8 is embossed in a checkerboard manner 260, the checkerboard consisting of squares the 90° angles of which pointing downward towards the center C of the pouch. The size of the individual squares may be in the range of from 0.01 to 10 mm$^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

Figure 11A:
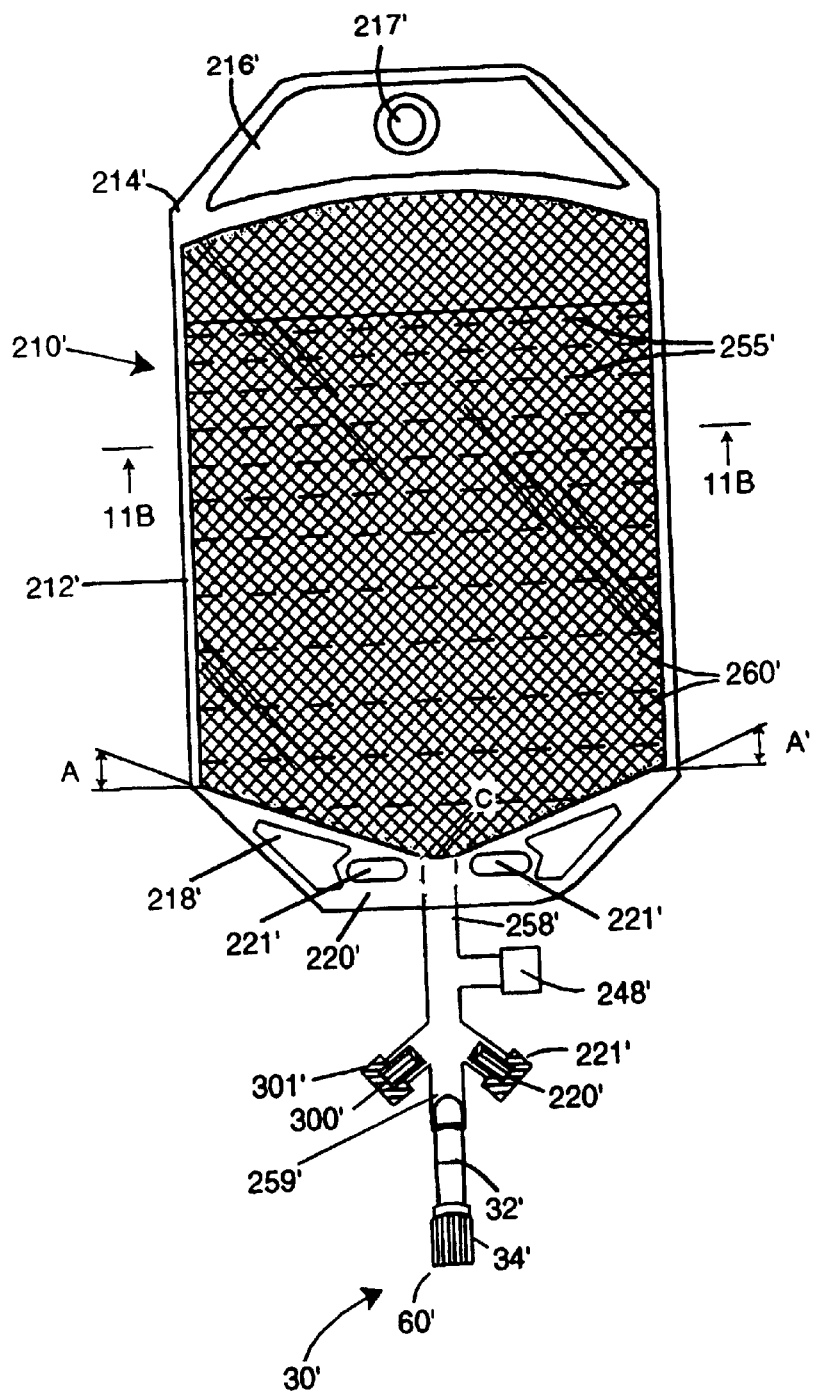
FIG. 11A is a plan view of the universal, flexible container shown in FIG. 9 one wall of which is embossed in a checkerboard fashion.
Figure 11B:
FIG. 11B is a cross-section of the universal, flexible container shown in FIG. 11A taken along the line 11B—11B.

FIG. 11A and FIG. 11B show the embodiment described in FIG. 9, except that the inside wall of first sheet of pouch 210' is embossed as described in FIGS. 10A and 10B.

Figure 12A:
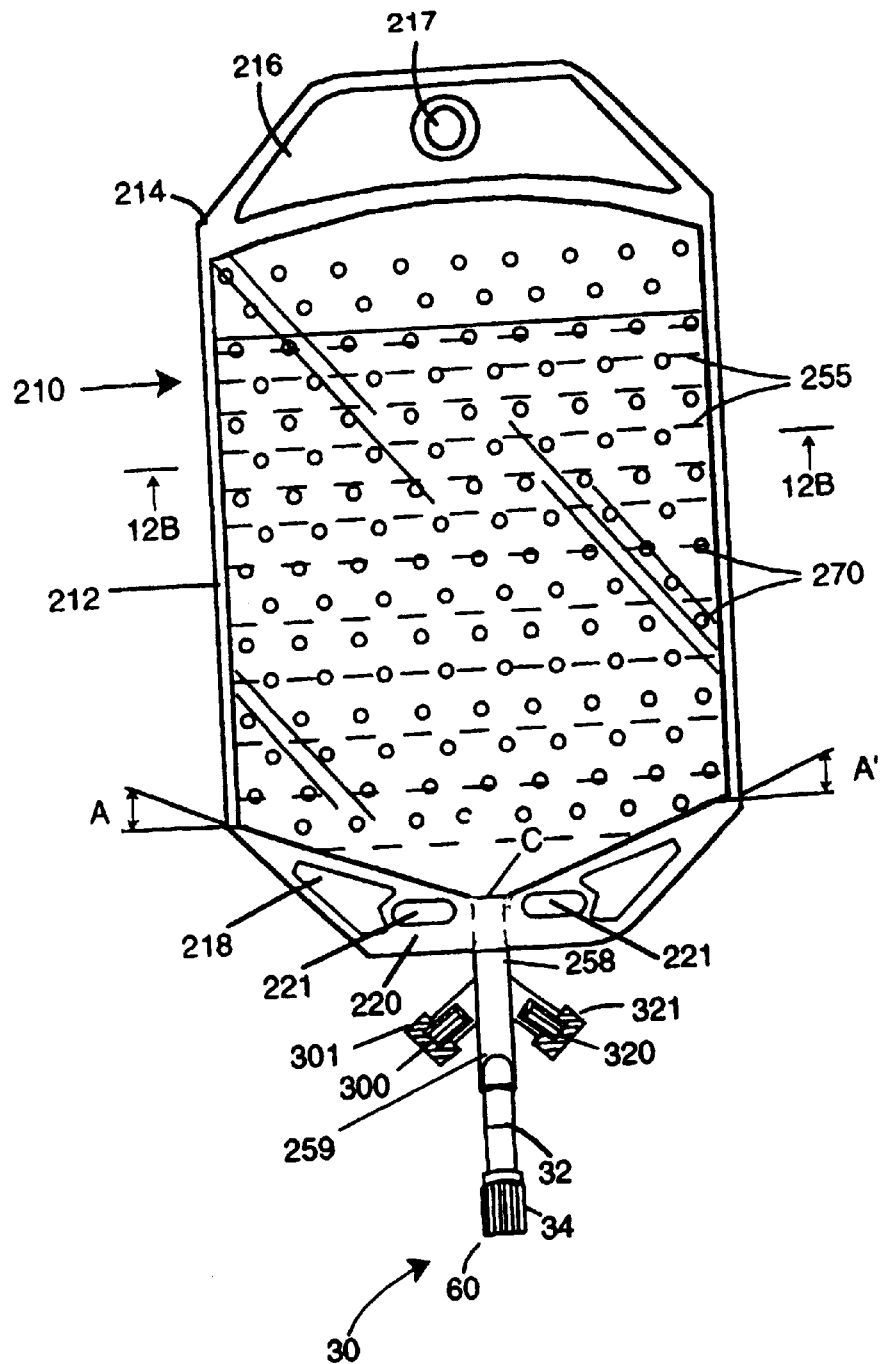
FIG. 12A is a plan view of the universal, flexible container shown in FIG. 8 one wall of which is embossed in a dotted fashion.
Figure 12B:
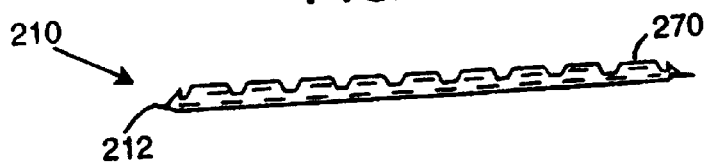
FIG. 12B is a cross-section of the universal, flexible container shown in FIG. 12A taken along the line 12B—12B.

Referring to FIG. 12A and FIG. 12B, the inside wall of first sheet of pouch 210 of FIG. 8 is embossed with dots or micro circles 270 in a spaced relationship from each other. The dots or circles may vary in diameter from 5 microns to several mms and may be spaced from each other of from about 10 microns to about 1 mms or longer. While both inside walls of the first sheet and second sheet may be embossed, it is preferred that only the first sheet or second sheet be embossed.

Figure 13A:
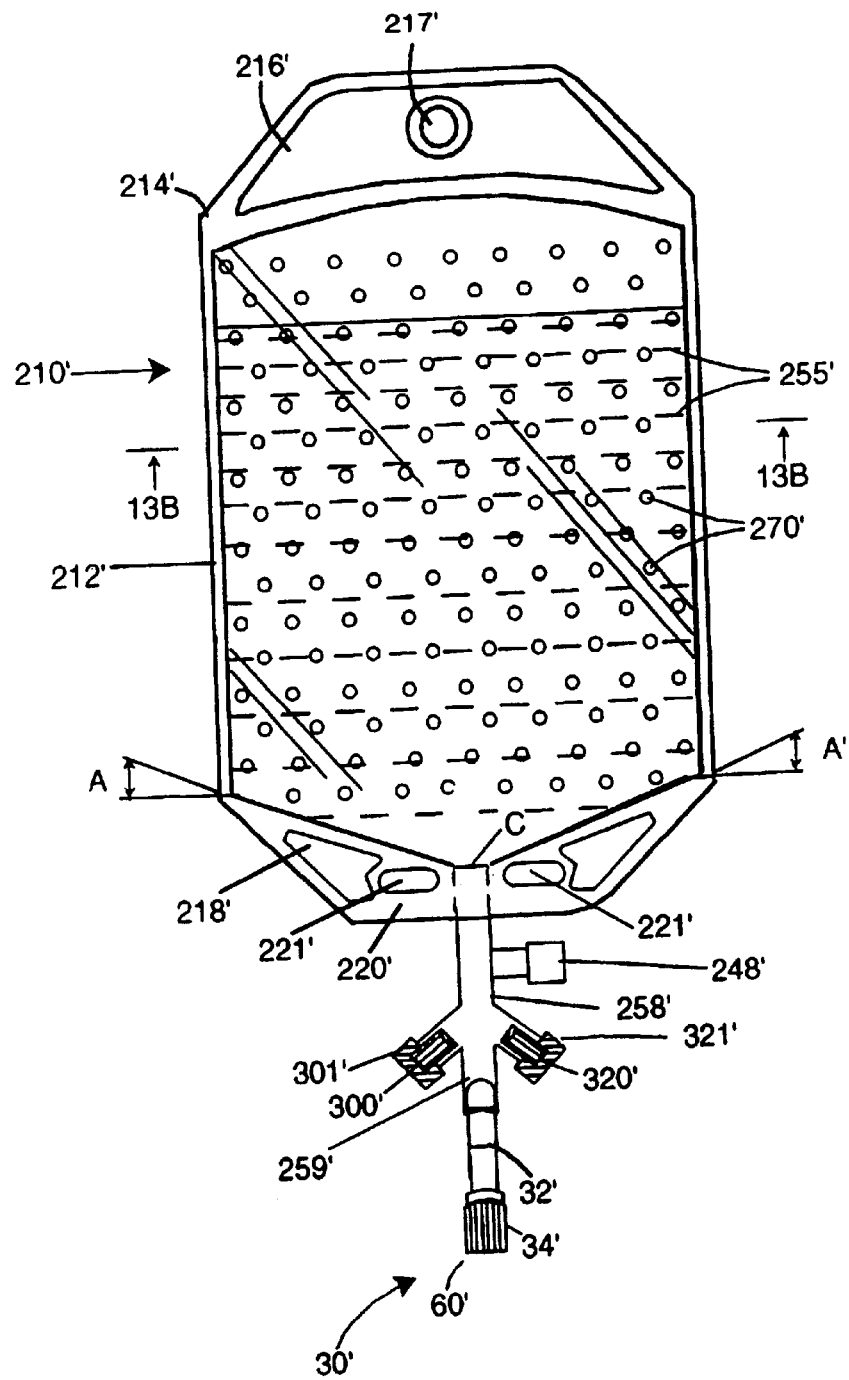
FIG. 13A is a plan view of the universal, flexible container shown in FIG. 9 one wall of which is embossed in a dotted fashion.
Figure 13B:
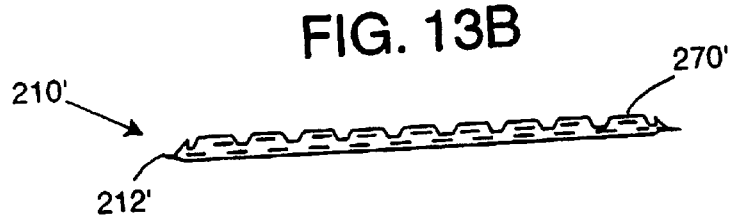
FIG. 13B is a cross-section of the universal, flexible container shown in FIG. 13A taken along the line 13B—13B.

FIG. 13A and FIG. 13B show the embodiment described in FIG. 9, except that the inside wall of first sheet of pouch 210' is embossed 270' as described in FIGS. 12A and 12B.

Figure 14A:
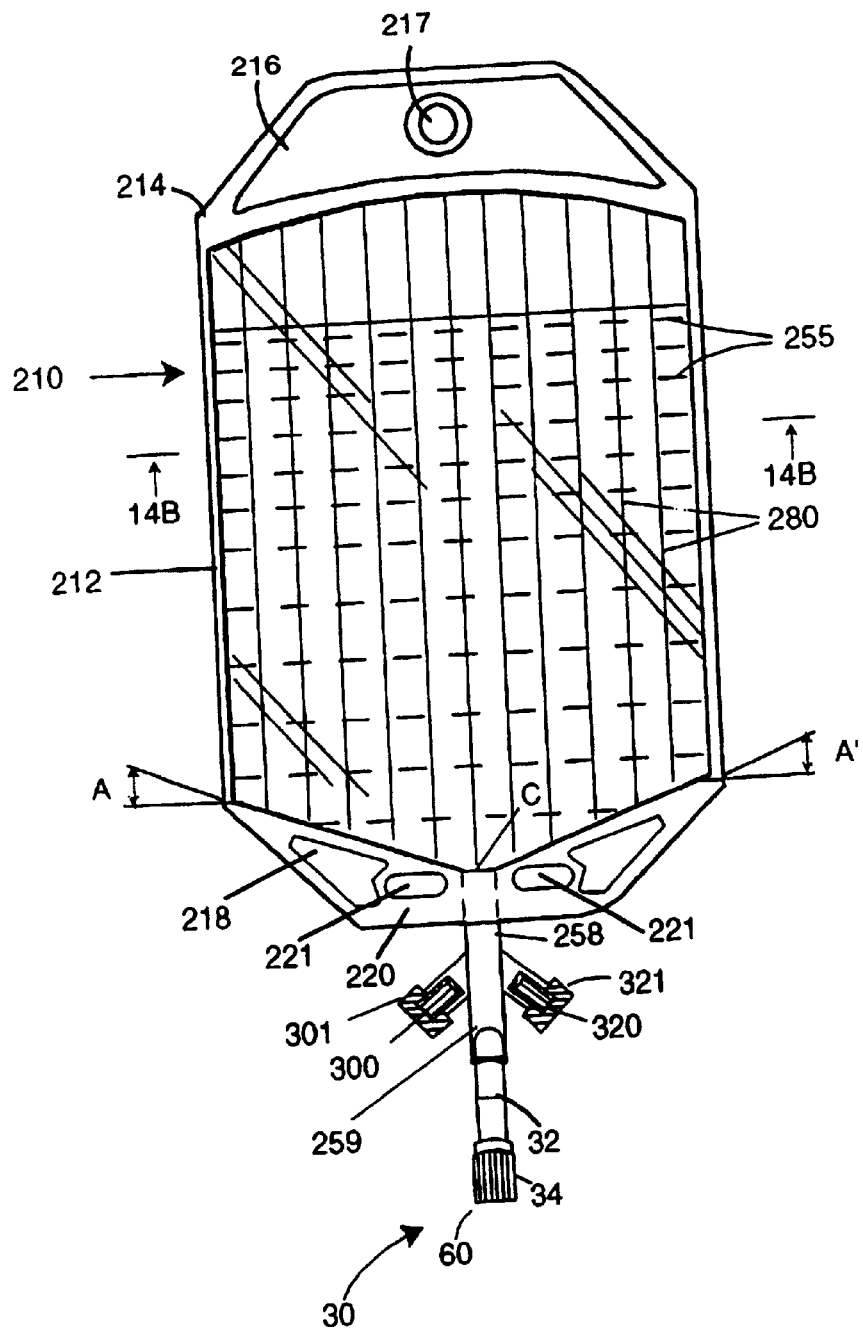
FIG. 14A is a plan view of the universal, flexible container shown in FIG. 8 one wall of which is embossed with vertically oriented channels.
Figure 14B:
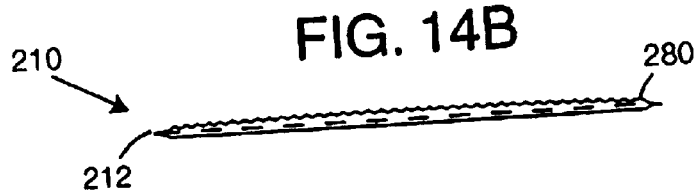
FIG. 14B is a cross-section of the universal, flexible container shown in FIG. 14A taken along the line 14B—14B.

Referring to FIGS. 14A and 14B, the inside wall of first sheet of pouch 210 shown in FIG. 8 is embossed 280 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

Figure 15A:
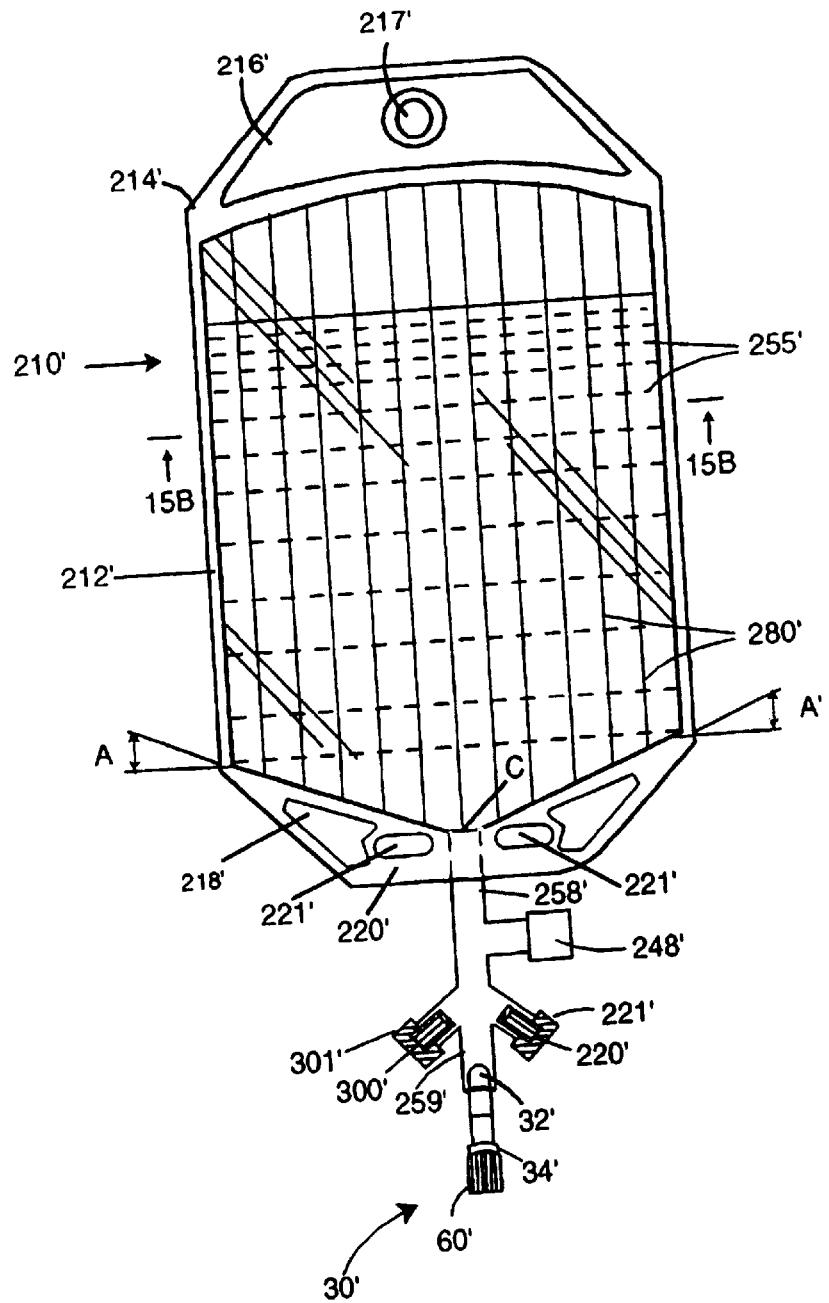
FIG. 15A is a plan view of the universal, flexible container shown in FIG. 9 one wall of which is embossed with vertically oriented channels.
Figure 15B:
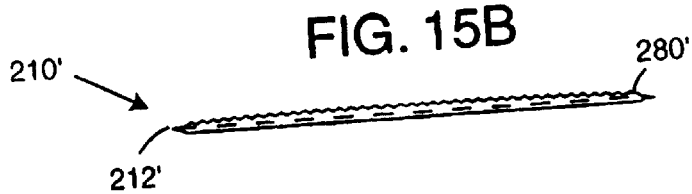
FIG. 15B is a cross-section of the universal, flexible container shown in FIG. 15A taken along the line 15B—15B.

FIG. 15A and FIG. 15B show the embodiment described in FIG. 9, except that the inside wall of first sheet of pouch 210' is embossed 280' as described in FIGS. 14A and 14B.

Referring to FIG. 16A and FIG. 16B, the inside wall of first sheet of pouch 210 of FIG. 8 is embossed 290 with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

Figure 17A:
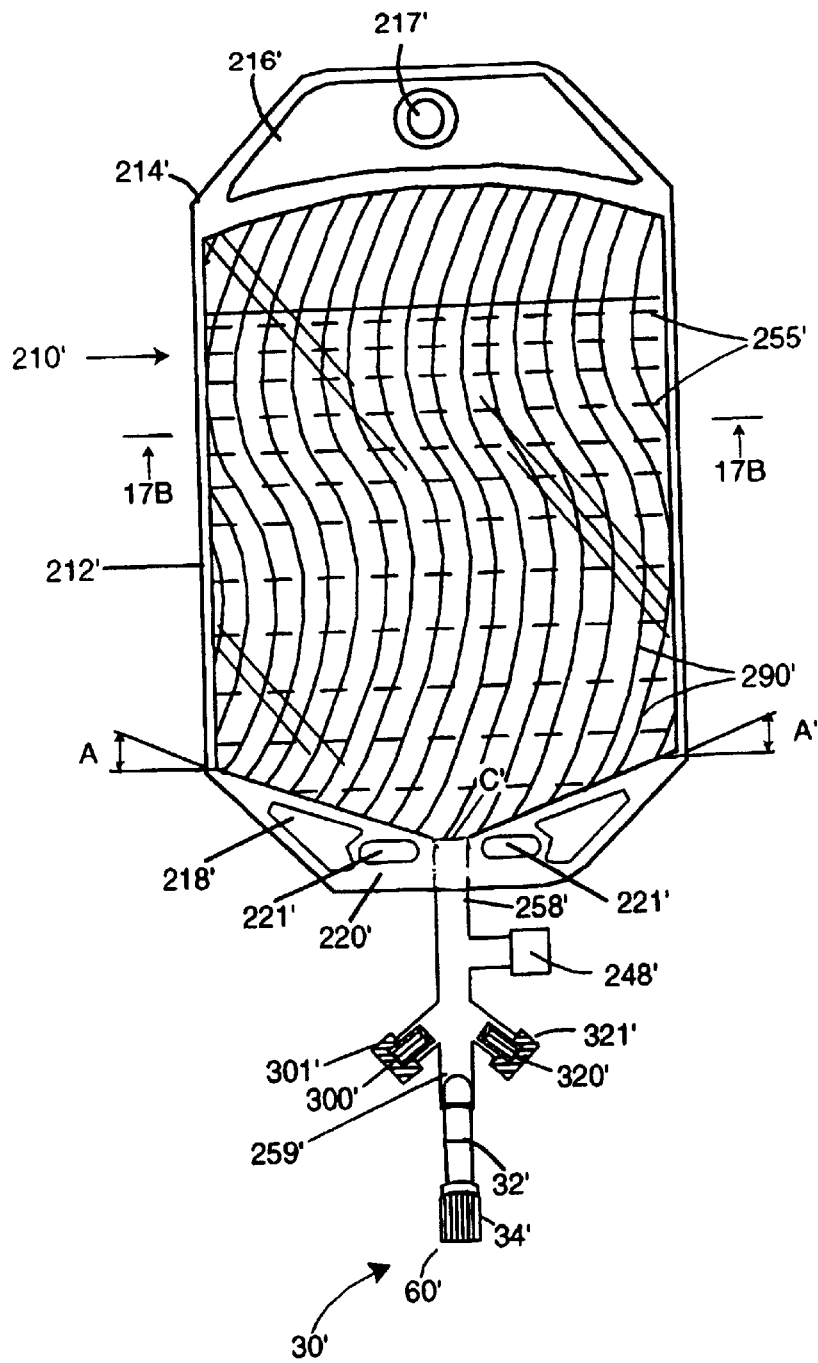
FIG. 17A is a plan view of the universal, flexible container shown in FIG. 9 one wall of which is embossed with vertically oriented S-shape channels.
Figure 17B:
FIG. 17B is a cross-section of the universal, flexible container shown in FIG. 17A taken along the line 17B—17B.

FIG. 17A and FIG. 17B show the embodiment described in FIG. 9, except that the inside wall of first sheet of pouch 210' is embossed 290' as described in FIGS. 16A and 16.

The sheets used in the present invention may be embossed with the described configuration by techniques known in the art. Alternatively, the layer constituting the internal liquid contacting layer of the sheet may be embossed prior to forming the multilayer sheets.

Process of Making and Using the Container

The flexible plastic container in the form of a bag, pouch or bottle is made of two rectangular sheets of polymeric materials one of which is embossed and flat welded together on four sides so as to defme between the two sheets and the four welded sides a reservoir. The volume of the container is zero before it is filled and typically has an internal volume capacity of from about 50 to about 5,000 ml when it is filled with a medical fluid, such as a parenteral solution.

Combination access member 258 or 258', needle access port 300 or 300', and spike access port 320 or 320' can be made by blow molding or other techniques known in the art. IV access port, vent 248 or 248' and the materials of construction of the single use universal connector are available from commercial sources.

Combination access member 258 or 258' are sealed between the superimposed sheets by the same welding process used to seal the superimposed sheets together. Upon completion of the welding process the container is suspended via holes 221 or 221', followed by filling the container through single use universal connector 30 with the desired fluid. Alternatively, the container may be sealed by heat welding at its four edges except at its bottom center portion C or C' and filled with the desired fluid prior to scaling combination access member 258 or 258' between the superimposed sheets. With either process, the universal, flexible container of the present invention, when it is filled with the desired fluid, provides for instant delivery via IV, needle or spike.

In the process of delivering the medical fluid to a patient using the IV access port having the single use universal connector thereon, the container 210 or 210' is suspended via hole 217 or 217', cap 60 is removed and a luer connector is engaged with the single use universal connector. Vent 248 or 248' allows outside air to replace the drained medical fluid in the container so that fluid flow is steady and continuous. If fluid delivery is desired using the needle or spike access ports, the container is suspended via hole 217 or 217', caps 201 or 201' or 221 or 221' are removed and needle or spike is inserted into the respective ports to enable delivery of the medical fluid to the desired site on the patient.

In the second embodiment the present invention provides a universal, flexible plastic container, in the shape of a bag, pouch or bottle, for the containment and delivery of diagnostic contrast media, nutrients and drug formulations. In the drawings where like numerals indicate like elements or portions, the reference character 310 and 310' in FIGS. 18 and 19 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 355 in FIG. 18 and 355' in FIG. 19, it assumes the shape of a small cushion. The superimposed sheets are joined together along marginal areas 312, 312', 314, 314', 316, 316', 318, 318', 320 and 320' as shown in FIGS. 18 and 19 respectively.

The bottom portion of pouch 310 or 310' terminates in first angle A and second angle A' from the center C or C' of said bottom portion and relative to a horizontal plane crossing the center C or C' of said bottom portion to direct and facilitate the flow of content contained in the pouch towards an IV access port 330 or 330', needle access port 400 or 400', and spike access port 420 or 420'. Angles A and A' are of from about 5° to about 45°, preferably from 10° to 30° and most preferably form 10 to 20 °.

Marginal areas 316 and 316' in FIGS. 18 and 19 preferably comprise at least one hole 317 or 317' for suspending the pouch when it is in use for delivering the content of the pouch to a delivery site.

Marginal areas 320 and 320' in FIGS. 18 and 19 preferably comprise at least one, and more preferably a plurality, of hole(s) 321 and 321' to facilitate suspending the pouch during the filling process.

Referring again to FIGS. 18 and 19, on one side of the IV access port there is located needle access port 400 or 400', which is integral with pouch 410 or 410', sealed between the superimposed sheets at the time of manufacture of the pouch 410 or 410'. Needle access port 410 or 410', having proximal end 402 or 402' and distal end 404 or 404' is equipped at its distal end with crimp seal 406 or 406'. Access to the needle access port 400 or 400' using a steel needle is gained by severing crimp seal 406 or 406'.

On the other side of the IV access port there is located spike access port 420 or 420', which is also integral with pouch 410 or 410', sealed between the superimposed sheets at the time of manufacture of the pouch 410 or 410'. Spike access port 420 or 420', having proximal end 422 or 422', is equipped at its distal end 424 and 424' with crimp seal 426 or 426'. Access to the spike access port 420 or 420', using a plastic spike, is gained by severing crimp seal 426 or 426'.

Needle access port 400 or 400' and spike access port 420 or 420' are positioned in the proximity of the IV access port, which positioning in combination with the bottom portion of pouch 410 or 410', having angle A or A', minimizes fluid waste/fluid hold up.

The container of the present invention may be used for delivering a single dose or multi-dose of parenteral solution. The needle and spike ports, along with the IV access port, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was discovered that if the inside wall of the first sheet or the second sheet forming the pouch 410 of FIG. 18 or pouch 410' of FIG. 19 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Referring to FIG. 20A and FIG. 20B, the inside wall of first sheet of pouch 310 shown in FIG. 18 is embossed in a checkerboard manner 360, the checkerboard consisting of squares the 90° angles of which pointing downward towards the center C of the pouch. The size of the individual squares may be in the range of from 0.01 to 10 mm$^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

FIG. 21A and FIG. 21B show the embodiment described in FIG. 19, except that the inside wall of first sheet of pouch 310' is embossed as described in FIGS. 20A and 20B.

Referring to FIG. 22A and FIG. 22B, the inside wall of first sheet of pouch 310 of FIG. 18 is embossed with dots or micro circles 370 in a spaced relationship from each other. The dots or circles may vary in diameter from 5 microns to several mms and may be spaced from each other of from about 10 microns to about 10 mms or longer. While both inside walls of the first sheet and second sheet may be embossed, it is preferred that only the first sheet or second sheet be embossed.

FIG. 23A and FIG. 23B show the embodiment described in FIG. 19, except that the inside wall of first sheet of pouch 310' is embossed 370' as described in FIGS. 22A and 22B.

Referring to FIG. 24A and FIG. 24B, the inside wall of first sheet of pouch 310 shown in FIG. 18 is embossed 380 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

FIG. 25A and FIG. 25B show the embodiment described in FIG. 19, except that the inside wall of first sheet of pouch 310' is embossed 380' as described in FIGS. 24A and 24B.

Referring to FIG. 26A and FIG. 26B, the inside wall of first sheet of pouch 310 of FIG. 18 is embossed 390 with vertically oriented channels which have a slight S-shape configuration in a spaced relationship from each other. The size of the width of individual channels may be in the range of from about 0.01 to about 1 mms or larger. The channels may be spaced from each other of from about 10 microns to about 10 mms. While both inside walls of the first sheet and second sheet may be embossed, it is preferred that only one inside wall of the first or second sheet be embossed.

FIG. 27A and FIG. 27B show the embodiment described in FIG. 19, except that the inside wall of first sheet of pouch 310' is embossed 390' as described in FIGS. 26A and 26B.

Materials of Construction

The flexible container of the various embodiments of the present invention is made of known polymeric materials having properties which make them suitable for sterile delivery of parenteral liquids. The sheets for forming the walls of the container are preferably multilayer sheets and characterized by heat resistance, gloss, strength, flexibility, and chemical inertness. Preferably the sheets are transparent or at least translucent enabling visual inspection of the contents at all times during delivery of content form the container to the patient. The container must be sterilizable, preferably by heat, along with its content. At least one layer of the sheet must be impervious to atmospheric gases and to steam. Preferably, the internal surface of the pouch in contact with the parenteral solution therein should be impervious to gas and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylacetate layers. The polyvinylidene chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20(g/m$^2$/day at 38° C., 100%RH); and an oxygen barrier of 650 (cc/m$^2$/day at 23° C., 0% RH, bar. CRYOVAC® sterlizable medical films (W. R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250kg/cm$^2$; a moisture vapor transmission rate of 5 (g/m$^2$/day at 38° C., 100%RH); and an oxygen barrier of about 1500 (cc/m$^2$/day at 23° C., 0%RH, bar).

Other polymeric films or sheets for constructing the universal, flexible container of the present invention include: copolyester ether monolayer films, such as polycyclohexanedimethylcyclohexane, dicarboxylate elastomer made by Eastman Kodak Co.; and ethyl vinyl acetate made by Stedim, Inc. It is important that the fluid contacting layer of the multilayer sheet contain no plasticizer which may contaminate the fluid content of the container.

Preferably, no plasticizer should be used at all on any of the multilayers to form the universal, flexible container of the present invention.

The sheets used in the present invention may be embossed with the described configuration by techniques known in the art. Alternatively, the layer constituting the internal liquid contacting layer of the sheet may be embossed prior to forming the multilayer sheets.

Access ports used in the present invention may be made of polyvinyl chloride which are sold commercially for use in medical devices. Other port and tubing materials may also be used, such as CRYOVAC® Port Tubing (W. R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process of Making the Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution. Access ports 330 or 330', 402 or 402', and 422 or 422' are sealed by the same welding process used to seal the two superimposed layers of sheets together at the center C or C' of the container 310 or 310'. Upon completion of the welding process the container is suspended via holes 321 or 321', followed by filling the container through the IV access port with the desired medical fluid.

In the process of delivering the medical fluid to a patient using the IV access port equipped with the single use universal connector, the container 310 or 310' is suspended via hole 317 or 137', cap 60 or 60' is removed and one way luer slip assembly is engaged with the single use universal connector. Vent 348 or 348' allows outside air to replace the drained medical fluid in the container so that fluid flow is steady and continuous. If fluid delivery is desired using the needle or spike access ports, the container is suspended via hole 317 or 317', crimp seal 406 or 406' or 426 or 426' is severed and needle or spike is inserted into the respective ports to enable delivery of the medical fluid to the desired site on the patient.

LIST OF REFERENCE NUMBERS USED

| | |
|---|---|
| Intravenous infusion bag (IV bag) | 10 |
| Fluid contained in bag | 12 |
| Fluid exit port or tube in IV bag | 14 |
| Distal end of fluid exit port or tube | 16 |
| Proximal end of fluid exit port or tube | 18 |
| Bottom seam of IV bag | 20 |
| Universal connector | 30 |
| Distal end of universal connector | 32 |
| Proximal end of universal connector | 34 |
| Inside wall of universal connector | 36 |
| Outside wall of universal connector | 38 |
| First cap-locking ring | 40 |
| Proximal end of second locking-ring | 41 |
| Second cap-locking ring | 42 |
| Distal end of inside wall of universal connector | 50 |
| Proximal end of inside wall of universal connector | 52 |
| Side wall of cylindrical opening at proximal end of universal connector | 54 |
| Bottom wall of cylindrical opening at proximal end of universal connector | 56 |
| Cylindrical cap of universal connector | 60 |
| Internal threads on cap | 66, 66' |
| Bottom wall of cap | 68 |
| Top wall of cap | 70 |
| Plug | 71 |
| Central portion of top wall | 72 |
| Side wall of plug | 74 |
| Bottom wall of plug | 76 |
| Outside wall of cylindrical protuberance of cap | 78 |
| Bottom wall of cylindrical protuberance of cap | 80 |
| Shoulder connecting inside wall of cap and outside wall of cylindrical protuberance of cap | 82 |
| Elastomeric membrane | 90, 92, 100, 110 |
| Dome-shape configuration in center of elastomeric membrane | 94 |
| Horizontal portion of dome-shape membrane | 96 |
| Cone-shape configuration of elastomeric membrane 100 | 102 |
| Horizontal portion of cone-shape membrane 102 | 104 |
| Conic section in elastomeric membrane 110 | 112 |
| Horizontal portion of elastomeric membrane 110 | 114 |
| Female luer connector | 120 |
| Cylindrical cap of female luer connector | 130 |
| Top portion of cylindrical cap | 138 |
| Center top portion of cylindrical cap | 140 |
| Wall portion of cylindrical cap facing tubing conduit 150 | 144 |
| Tubing conduit in female luer connector | 150 |
| Outside wall of tubing conduit | 152 |
| Inside wall of tubing conduit | 154, 154' |
| Fluid channel | 156 |
| Bottom end portion of tubing conduit | 158 |
| First Preferred Embodiment | |
| Universal connector | 30, 30' |
| Distal end of universal connector | 32, 32' |
| Proximal end of universal connector | 34, 34' |
| Cap of universal connector | 60, 60' |
| Pouch (formed by superimposed sheets) | 210, 210' |
| Sealed marginal areas | 212, 212', 214, 214', 216, 216', 218, 218', 220, 220' |
| Proximal end of access member — inverted Y shape configuration | 258, 258' |
| Distal end of access member | 259, 259' |
| Tines — needless access port | 300, 300' |
| Tines — spike access port | 320, 320' |
| Cap to cover spike access port | 301, 301' |
| Cap to cover spike access port | 321, 321' |
| Vent | 248, 248' |
| Plurality of holes to suspend pouch during the filing process | 221, 221' |
| Plurality of holes to suspend pouch when delivering its content to a site | 217, 217' |
| Checkerboard embossment | 260, 260' |
| Dots or microcircles embossment | 270, 270' |
| Vertical channel embossment | 280, 280' |
| S-shape configuration embossment | 290, 290' |
| Second Preferred Embodiment | |
| Pouch | 310, 310' |
| Sealed marginal areas | 312, 312', 314, 314', 316, 316', 318, 318', 320, 320' |
| Holes for suspending pouch when delivering content to a site | 317, 317' |
| Holes for suspending pouch during the filling process | 321, 321' |
| IV access port | 330, 330' |
| Needle access port | 400, 400' |
| Proximal end of needle access member | 402, 402' |
| Distal end of access member | 404, 404' |
| Crimp seal on needle access port | 406, 406' |
| Spike access port | 420, 420' |
| Proximal end of spike access port | 422, 422' |
| Distal end of spike access port | 424, 424' |

-continued

| | |
|---|---|
| Crimp seal on spike access port | 426, 426' |
| Checkerboard embossment | 360, 360' |
| Dots or microcircles embossment | 370, 370' |
| Vertical channel embossment | 380, 380' |
| S-shape configuration embossment | 390, 390' |

Various modifications of the several embodiments disclosed will become apparent to those skilled in the art. The invention is intended to include such modifications to be limited only by the scope of the claims.

What is claimed is:

1. A single use universal connector, flexible medical container assembly for the containment and delivery of a medical fluid comprising:
a) a flexible medical container having first and second polymeric sheets having a square, round, oval, hexagonal, octagonal or rectangular configuration superimposed and sealed together at their periphery to form a pouch defining an interior reservoir having an inside wall, said pouch having a top portion and a bottom portion with a center therein;
said bottom portion terminates in a first angle and a second angle of from about 5° to about 45° each from the center thereof and relative to a horizontal plane crossing the center of said bottom portion;
portions of said interior reservoir being mechanically or chemically embossed;
b) a combination access member of inverted Y shape configuration having:
b1) a stem with a proximal end and a distal end, said proximal end located at the bottom, center portion of the pouch sealed between said first and second polymeric sheets; and
b2) a pair of tines having proximal and distal ends, the proximal ends thereof being integral with the stem of the access member; the combination access member comprising:
(1) an IV access port having a distal end and a proximal end, said proximal end being sealably attached to said distal end of the stem, and said distal end being sealably attached to a single use universal connector, said single use universal connector comprising:
(1a) a connector body of tube-like configuration having a distal end and a proximal end, wherein said proximal end is slideably inserted into the distal end of said IV access port and said distal end is sealed by an elastomeric membrane and a removable cap;
(1b) an elastomeric membrane of an inert, gas-impermeable polymeric material, capable of flexing under pressure, sealing said distal end of said single use universal connector body; and
(1c) a removable cap threaded onto the distal end of said single use universal connector body to protect said elastomeric membrane from environmental forces and maintain said elastomeric membrane in aseptic condition prior to removal of said cap;
(2) a needle access port located in one of the tines of the combination access member; and
(3) a spike access port located in the other of the tines of the combination access member;
said needle and spike access ports being equipped with caps.

2. The single use universal connector, flexible medical container assembly of claim 1 wherein said connector body further comprises:
(1) a first cap-locking ring on the proximal end of said connector body which serves as a male thread to receive said removable cap; and
(2) a second cap-locking ring, spaced from said first cap-locking ring towards the distal end of said connector body, which serves as stopping means for the removable cap when the removable cap is threaded onto the connector body.

3. The single use universal connector, flexible medical container assembly of claim 1 wherein said combination access member further comprises a vent.

4. The single use universal connector, flexible medical container assembly of claim 1 wherein said elastomeric membrane has a thickness of from about 0.001 mm and a durometer of from about 25 to about 80 Shore A.

5. The single use universal connector, flexible medical container assembly of claim 1 wherein said elastomeric membrane is of an elastomeric material selected from the group consisting of:
natural rubber;
acrylate-butadiene rubber;
cis-polybutadiene;
chlorobutyl rubber;
chlorinated polyethylene elastomer;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

6. The single use universal connector, flexible medical container assembly of claim 1 wherein said elastomeric membrane is cylindrical, dome-shape, cone-shape or conical configuration.

7. The single use universal connector, flexible medical container assembly of claim 1 wherein the inside wall of said interior reservoir is embossed in a checkerboard fashion.

8. The single use universal connector, flexible medical container assembly of claim 1 wherein the inside wall of said interior reservoir is embossed with micro circles or dots.

9. The single use universal connector, flexible medical container assembly of claim 8 wherein said micro circles or dots have a diameter of at least 5 microns and are spaced form each other of from about 10 microns to about 10 millimeters.

10. The single use universal connector, flexible medical container assembly of claim 1 wherein the inside wall of said interior reservoir is embossed with vertical channels in spaced relationship from each other and oriented in a length-wise direction of the pouch.

11. The single use universal connector, flexible medical container assembly of claim 10 wherein the width of each of said channels is of from about 0.01 to about 10 millimeters and said channels are spaced from each other of from about 10 microns to about 10 millimeters.

12. The single use universal connector, flexible medical container assembly of claim 1 wherein the inside wall of said interior reservoir is embossed with vertically oriented S-shaped channels in spaced relationship from each other and oriented in a length-wise direction.

13. The single use universal connector, flexible medical container assembly of claim 12 wherein the width of each of said S-shape channel is of from about 0.01 to about 10 millimeters and said channels are spaced from each other of from about 10 microns to about 10 millimeters.

14. The single use universal connector, flexible medical container assembly of claim 1 wherein said first and second polymeric sheets are made of polyvinylidene chloride sandwiched between two layers of polyethylene or polyvinylacetate.

15. The single use universal connector, flexible medical container assembly of claim 1 wherein said first and second polymeric sheets are made of polyvinyl chloride.

16. The single use universal connector, flexible medical container assembly of claim 1 wherein said first and second polymeric sheets are made of a polyethylene layer sandwiched between polyester outer layers sealed together by a propylene copolymer.

17. The single use universal connector, flexible medical container assembly of claim 1 wherein said first and second polymeric sheets are made of polycyclohexanedimethylcyclohexane dicarboxylate.

18. The single use universal connector, flexible medical container assembly of claim 1 wherein said first and second polymeric sheets are made of ethyl vinyl acetate.

19. The single use universal connector, flexible medical container assembly of claim 1 wherein said first and second polymeric sheets are made of polyvinylidene chloride sandwiched between two layers of polyethylene or polyvinylacetate.

20. A single use universal connector, flexible medical container assembly for the containment and delivery of a medical fluid comprising:
   a) a flexible medical container having first and second polymeric sheets having a square, round, oval, hexagonal, octagonal or rectangular configuration superimposed and sealed together at their periphery defining an interior reservoir having an inside wall, said flexible medical container having a top portion and a bottom portion with a center therein;
   said bottom portion terminates in a first angle and a second angle of from about 5° to about 45° each from the center thereof and relative to a horizontal plane crossing the center of said bottom portion; portions of said interior reservoir being mechanically or chemically embossed;
   b) a first access member integral with said flexible medical container located at the center of said bottom portion allowing filling of the flexible medical container with a medical fluid and access thereto for delivery to a patient, said access member comprising:
      an access port located below the bottom portion of said flexible medical container where said first angle and said second angle meet, said access port sealably attached to a single use universal connector, said single use universal connector comprising:
         a connector body of tube-like configuration having a distal end and a proximal end, wherein said proximal end is slideably inserted into said access port and sealed thereinto, and said distal end is sealed by an elastomeric membrane and a removable cap;
         an elastomeric membrane of an inert, gas-impermeable polymeric material, capable of flexing under pressure, sealing said distal end of said single use universal connector body; and
         a removable cap threaded onto the distal end of said single use universal connector body to protect said elastomeric membrane from environmental forces and maintain said elastomeric membrane in aseptic condition prior to removal of said cap to access a medical fluid contained in said flexible medical container or to transfer a medical fluid to said container by an access or a transfer means;
   c) a second access member comprising a needle access port located on one side and adjacent to said first access member in the bottom portion of said flexible medical container; and
   d) a third access member comprising a spike access port located on the other side and adjacent to said first access member in the bottom portion of said flexible medical container,
   said needle and spike access ports being equipped with caps to seal said medical fluid in said flexible medical container.

21. The single use universal connector, flexible medical container assembly of claim 20 wherein said connector body further comprises:
   (1) a first cap-locking ring on the proximal end of said connector body which serves as a male thread to receive said removable cap; and
   (2) a second cap-locking ring, spaced from said first cap-locking ring towards the distal end of said connector body, which serves as stopping means for the removable cap when the removable cap is threaded onto the connector body.

22. The single use universal connector, flexible medical container assembly of claim 20 wherein said first access member further comprises a vent.

23. The single use universal connector, flexible medical container assembly of claim 20 wherein said elastomeric membrane has a thickness of from about 0.001 mm and a durometer of from about 25 to about 80 Shore A.

24. The single use universal connector, flexible medical container assembly of claim 20 wherein said elastomeric membrane is of an elastomeric material selected from the group consisting of:
   natural rubber;
   acrylate-butadiene rubber;
   cis-polybutadiene;
   chlorobutyl rubber;
   chlorinated polyethylene elastomers;
   polyalkylene oxide polymers;
   ethylene vinyl acetate;
   fluorosilicone rubbers;
   hexafluoropropylene-vinylidene fluoride-tetrafluoroethylene terpolymers;
   butyl rubbers;
   polyisobutene;
   synthetic polyisoprene rubber;
   silicone rubbers;
   styrene-butadiene rubbers;
   tetrafluoroethylene propylene copolymers; and
   thermoplastic-copolyesters.

25. The single use universal connector, flexible medical container assembly of claim 20 wherein said elastomeric membrane is cylindrical, dome-shape, cone-shape or conical configuration.

26. The single use universal connector, flexible medical container assembly of claim 20 wherein the inside wall of said interior reservoir is embossed in a checkerboard fashion.

27. The single use universal connector, flexible medical container assembly of claim 20 wherein the inside wall of said interior reservoir is embossed with micro circles or dots.

28. The single use universal connector, flexible medical container assembly of claim 27 wherein said micro circles or dots have a diameter of at least 5 microns and are spaced from each other of from about 10 microns to about 10 millimeters.

29. The single use universal connector, flexible medical container assembly of claim 20 wherein the inside wall of said interior reservoir is embossed with vertical channels in spaced relationship from each other and oriented in a length-wise direction.

30. The single use universal connector, flexible medical container assembly of claim 29 wherein the width of each of said channels is of from about 0.01 to about 10 millimeters and said channels are spaced from each other of from about 10 microns to about 10 millimeters.

31. The single use universal connector, flexible medical container assembly of claim 20 wherein the inside wall of said interior reservoir is embossed with vertically oriented S-shaped channels in spaced relationship from each other and oriented in a length-wise direction.

32. The single use universal connector, flexible medical container assembly of claim 23 wherein the width of each of said S-shape channel is of from about 0.01 to about 10 millimeters and said channels are spaced from each other of from about 10 microns to about 10 millimeters.

33. The single use universal connector, flexible medical container assembly of claim 20 wherein said first and second polymeric sheets are made of polyvinyl chloride.

34. The single use universal connector, flexible medical container assembly of claim 20 wherein said first and second polymeric sheets are made of a polyethylene layer sandwiched between polyester outer layers sealed together by a propylene copolymer.

35. The single use universal connector, flexible medical container assembly of claim 20 wherein said first and second polymeric sheets are made of polycyclohexanedimethylcyclohexane dicarboxylate.

36. The single use universal connector, flexible medical container assembly of claim 20 wherein said first and second polymeric sheets are made of ethyl vinyl acetate.

\* \* \* \* \*